US009902749B2

(12) United States Patent
Kashimoto et al.

(10) Patent No.: US 9,902,749 B2
(45) Date of Patent: Feb. 27, 2018

(54) METALLOCENE COMPLEX AND OLEFIN POLYMERIZATION METHOD

(71) Applicant: JAPAN POLYPROPYLENE CORPORATION, Tokyo (JP)

(72) Inventors: Masami Kashimoto, Kanagawa (JP); Takayoshi Takahashi, Kanagawa (JP); Naoshi Iwama, Mie (JP); Masato Nakano, Mie (JP); Toshinori Suzuki, Mie (JP)

(73) Assignee: JAPAN POLYPROPYLENE CORPORATION, Tokyo (JP)

( * ) Notice: Subject to any disclaimer, the term of this patent is extended or adjusted under 35 U.S.C. 154(b) by 114 days.

(21) Appl. No.: 14/435,819

(22) PCT Filed: Oct. 28, 2013

(86) PCT No.: PCT/JP2013/079093
§ 371 (c)(1),
(2) Date: Apr. 15, 2015

(87) PCT Pub. No.: WO2014/069391
PCT Pub. Date: May 8, 2014

(65) Prior Publication Data
US 2015/0266914 A1 Sep. 24, 2015

(30) Foreign Application Priority Data

Nov. 1, 2012 (JP) .................................. 2012-241557
Sep. 13, 2013 (JP) .................................. 2013-190208

(51) Int. Cl.
*C07F 17/00* (2006.01)
*C08F 10/06* (2006.01)
*C08F 297/08* (2006.01)
*C08F 293/00* (2006.01)
*C08F 4/659* (2006.01)

(52) U.S. Cl.
CPC .............. *C07F 17/00* (2013.01); *C08F 10/06* (2013.01); *C08F 293/00* (2013.01); *C08F 297/083* (2013.01); *C08F 4/65912* (2013.01); *C08F 4/65916* (2013.01)

(58) Field of Classification Search
USPC .............................. 556/11, 51; 502/103, 117
See application file for complete search history.

(56) References Cited

U.S. PATENT DOCUMENTS

| | | | |
|---|---|---|---|
| 5,698,645 A | 12/1997 | Weller et al. | |
| 6,350,830 B1 | 2/2002 | Gores et al. | |
| 8,461,365 B2* | 6/2013 | Nakano | C07F 17/00 502/103 |
| 2001/0053833 A1 | 12/2001 | Nakano et al. | |
| 2003/0149199 A1 | 8/2003 | Schottek et al. | |
| 2004/0127731 A1 | 7/2004 | Ushioda et al. | |
| 2004/0260107 A1 | 12/2004 | Oberhoff et al. | |
| 2005/0154139 A1 | 7/2005 | Ishihara et al. | |
| 2006/0020096 A1 | 1/2006 | Schottek et al. | |
| 2010/0267907 A1 | 10/2010 | Dimeska et al. | |
| 2011/0230622 A1* | 9/2011 | Nakano | C07F 17/00 525/245 |
| 2011/0230630 A1 | 9/2011 | Sell et al. | |
| 2012/0329964 A1 | 12/2012 | Dimeska et al. | |
| 2014/0303332 A1 | 10/2014 | Yang et al. | |

FOREIGN PATENT DOCUMENTS

| | | |
|---|---|---|
| CN | 1120551 A | 4/1996 |
| CN | 102245620 A | 11/2011 |
| EP | 1052263 A2 | 11/2000 |
| EP | 2341087 A1 | 7/2011 |
| JP | 4-337308 A | 11/1992 |
| JP | 6-287257 A | 10/1994 |
| JP | 11-240909 A | 9/1999 |
| JP | 2001-011089 A | 1/2001 |
| JP | 2002-504569 A | 2/2002 |

(Continued)

OTHER PUBLICATIONS

Yong-Woo et al., "Synthesis and characterization of ethylene-propylene random copolymers with isotactic propylene sequence", Polymer, 2001, pp. 9611-9615, vol. 42.
International Search Report for application No. PCT/JP2013/079093, dated Jan. 21, 2014.
International Preliminary Report on Patentability for application No. PCT/JP2013/079093, dated May 5, 2015.
Chinese Office Action issued with respect to Application No. 201480011052.7, dated Dec. 1, 2016.
Extended European Search Report issued with respect to Application No. 16000898.3, dated Aug. 31, 2016.
Extended European Search Report issued with respect to Application No. 14757800.9, dated Oct. 21, 2015.
Karresnberg et al., "Terminal and Penultimate Reactivity Ratios in Single-Site Ethene/Propene Copolymerizations: Comparison of Kakugo and Direct Peak Methods", Macromol. Chem. Phys., 2005, pp. 206, 1675-1683.

(Continued)

*Primary Examiner* — Pancham Bakshi
(74) *Attorney, Agent, or Firm* — Greenblum & Bernstein, P.L.C.

(57) ABSTRACT

Provided are a metallocene complex that facilitates copolymerization of olefin monomers including propylene at a higher uptake rate of comonomers, i.e., ethylene and α-olefin, manufacture of a rubber component having a higher molecular weight, and manufacture of homopolypropylene having a higher melting point through homopolymerization of propylene, compared to traditional metallocene catalysts, and a method of olefin polymerization in the presence of such a metallocene complex. Also provided are, for example, a metallocene complex represented by general formula [I] (e.g., a metallocene complex having a substituent at position 6 of one or each indenyl ring and an optionally substituted furyl or thienyl group at position 2 of one or each indenyl ring), an olefin polymerization catalyst containing the metallocene complex, and a method of olefin polymerization involving olefin polymerization or copolymerization in the presence of the olefin polymerization catalyst.

10 Claims, No Drawings

(56) References Cited

FOREIGN PATENT DOCUMENTS

| JP | 2002-194016 A | 7/2002 |
|---|---|---|
| JP | 2003-206325 A | 7/2003 |
| JP | 2004-352707 A | 12/2004 |
| JP | 2007-505947 A | 3/2007 |
| JP | 2008-101034 A | 5/2008 |
| JP | 4288658 B2 | 7/2009 |
| JP | 4416507 B2 | 2/2010 |
| JP | 2010/163423 A | 7/2010 |
| JP | 2011-500800 A | 1/2011 |
| JP | 2011-144157 A | 7/2011 |
| JP | 4901043 B2 | 3/2012 |
| JP | 2012-121882 | 6/2012 |
| JP | 2012-513463 A | 6/2012 |
| JP | 2013-001737 A | 1/2013 |
| JP | 2015-42617 A | 3/2015 |
| WO | 2004/106351 A1 | 12/2004 |
| WO | 2011/080152 A1 | 7/2011 |

OTHER PUBLICATIONS

Tynys et al., "Ethylene-Propylene Copolymerisations: Effect of Metallocene Structure on Termination Reactions and Polymer Microstructure", Macromol. Chem. Phys., 2005, pp. 206, 1043-1056.

Spaleck et al., "The Influence of Aromatic Substituents on the Polymerization Behavior of Bridged Zirconocene Catalysts", Organometallics, 1994, pp. 13, 954-963.

Quijada et al., "The influence of the comonomer in the copolymerization of ethylene with a-olefins using C2H4[Ind] 2ZrCl2/methylaluminoxane as catalyst system", Macromol. Chem. Phys., 1996, pp. 197, 3091-3098.

International Search Report issued with respect to application No. PCT/JP2014/054676, dated Jun. 3, 2014.

International Preliminary Report on Patentability issued with respect to application No. PCT/JP2014/054676, dated Sep. 1, 2015.

Notification of Reasons for Refusal issued with respect to JP application No. 2013-190208, dated Feb. 21, 2017.

Chinese Office Action issued with respect to Application No. 201480057170.7, dated Feb. 14, 2017.

Chinese Office Action issued with respect to application No. 201380057170.7, dated Sep. 20, 2016.

Chinese office Action issued with respect to application No. 201380057170.7, dated Mar. 24, 2016.

Decision to Grant a Patent issued with respect to Application No. 2013-190208 dated Jun. 9, 2017, with Written Amendment previously filed Apr. 14, 2017.

* cited by examiner

METALLOCENE COMPLEX AND OLEFIN POLYMERIZATION METHOD

TECHNICAL FIELD

The present invention relates to metallocene complexes and methods of olefin polymerization, particularly to a metallocene complex having substituents at particular positions that facilitates manufacture of polypropylene having a high melting point, copolymerization of propylene with ethylene at a high ethylene uptake rate, and manufacture of an ethylene-propylene copolymer rubber component having a high molecular weight, and also to a method of olefin polymerization in the presence of such a metallocene complex.

BACKGROUND ART

Crystalline polypropylene, which has superior characteristics such as good mechanical properties and high chemical resistance, has been widely used in various plastic processing fields. Propylene homopolymers and random copolymers thereof with small amounts of α-olefins have high rigidity, but some of these polymers may have insufficient impact resistance.

Accordingly, attempts have been made to improve the impact resistance, including the addition of a rubber component such as an ethylene-propylene rubber (EPR) to a propylene homopolymer and the manufacture of an impact copolymer containing a rubber component through homopolymerization of propylene and subsequent copolymerization of propylene with ethylene or α-olefin. An increase in the content of the rubber component can improve the flexibility and impact resistance of the impact copolymer.

Another problem exists in that an impact copolymer prepared in the presence of a traditional Ziegler-Natta catalyst inevitably contains low-molecular-weight components (e.g., oligomers). According to recent trends, the impact copolymers have high flowability for further improvements in moldability.

Unfortunately, excess flowability of the rubber component results in the generation of larger amounts of low-molecular-weight components, which cause various problems, such as fumes and odors during processing, detrimental effects on smell and taste after processing, and promoted blocking due to high stickiness. A polymer with poor powder characteristics cannot be stably manufactured. A larger difference in average molecular weight between the crystalline polypropylene and the rubber component causes problems such as a high gel content in a molded product and a high linear expansion coefficient of the molded product.

Metallocene catalysts, which are different from traditional Ziegler-Natta catalysts, are known for use in the polymerization of propylene into isotactic polypropylene.

Similar catalysts are also known for use in the manufacture of impact copolymers through homopolymerization of propylene and subsequent copolymerization of propylene with ethylene (see, for example, PTLs 1 and 2). Also disclosed are impact copolymers having satisfactory rigidity and high impact resistance (see, for example, PTL 3).

To achieve high impact resistance, impact copolymers must have a lower glass transition temperature, for example. To satisfy this requirement, it is preferred to copolymerize propylene with ethylene or α-olefin such that their respective contents fall within certain ranges (see, for example, NPL 1).

Many transition metal compounds are known for use as components of metallocene catalysts. Also known are transition metal compounds that produce homopolypropylene having a high melting point to provide an impact copolymer with improved rigidity (see, for example, PTL 4).

Unfortunately, the manufacture of such an impact propylene copolymer in the presence of a metallocene catalyst has the following technical problems associated with the difference in reactivity between propylene and other comonomers.

Specifically, the copolymerization of propylene with ethylene or α-olefin after homopolymerization of propylene in the presence of a metallocene catalyst by a conventional process may result in a large difference between the ratio of propylene to ethylene or α-olefin contained in the gaseous composition in the polymerization atmosphere and the ratio of propylene units to ethylene or α-olefin units in the copolymer polymerized in that atmosphere. This may result in a smaller amount of ethylene or α-olefin component in the polymer. To manufacture a copolymer having a desired ethylene or α-olefin content, the gaseous monomers must be supplied and polymerized in a ratio that differs largely from that of the copolymer. Such control is disadvantageous for manufacture. In extreme cases, a copolymer having a desired ethylene or α-olefin content cannot be manufactured because of the restraints imposed by polymerization systems.

Accordingly, it is desirable to develop a method for manufacturing polypropylene at a high uptake rate of ethylene and α-olefin in the presence of a metallocene complex catalyst without involving a large difference in ethylene content between the gaseous ethylene/propylene mixture and the resulting polymer.

Another problem associated with traditional metallocene catalysts is production of a copolymer having a low molecular weight in gas-phase copolymerization of propylene with ethylene or α-olefin. To provide a propylene-ethylene block copolymer with high impact resistance, the resulting copolymer must also have a certain molecular weight. Accordingly, development of a method for manufacturing a copolymer having a high molecular weight is eagerly awaited. Also awaited is development of a catalyst having high rubber polymerization activity in order to decrease the catalyst cost per unit polymer and increase the rubber content.

As described above, homopolypropylene having a high melting point is required to provide an impact copolymer with improved rigidity. Unfortunately, among the above metallocene catalysts that have an improved uptake rate of ethylene and α-olefin and facilitate manufacture of a copolymer having a high molecular weight, a metallocene complex catalyst is yet to be known that sufficiently functions as a catalyst for manufacturing homopolypropylene having a high melting point.

PTL 5 discloses a metallocene complex having a substituent at position 5 of one or each indenyl ring and an optionally substituted furyl or thienyl group at position 2 of one or each indenyl ring. This metallocene complex has a high ethylene uptake rate and can provide a copolymer having a high molecular weight.

PTL 6 discloses an asymmetric metallocene complex having methyl groups at positions 5 and 6 and an alkyl group at position 2 of one of the indenyl rings. This metallocene complex has a high ethylene uptake rate and can provide a copolymer having a high molecular weight.

Unfortunately, the metallocene complexes disclosed in PTLs 5 and 6 are still unsatisfactory because they cannot produce homopolypropylene having a sufficiently high melting point. Accordingly, development of a metallocene complex with improved performance is eagerly awaited.

CITATION LIST

Patent Literature

PTL 1: Japanese Unexamined Patent Application Publication No. 4-337308
PTL 2: Japanese Unexamined Patent Application Publication No. 6-287257
PTL 3: Japanese Unexamined Patent Application Publication No. 2003-206325
PTL 4: Japanese Unexamined Patent Application Publication No. 11-240909
PTL 5: Japanese Unexamined Patent Application Publication No. 2010-163423
PTL 6: WO2004/106351 corresponding to Japanese Unexamined Patent Application Publication No. 2007-505947
Non Patent Literature
NPL 1: Polymer, 2001, vol. 42, p. 9,611

SUMMARY OF INVENTION

Technical Problem

In view of the foregoing problems associated with the related art, an object of the present invention is to provide a metallocene complex that facilitates copolymerization of olefin monomers including propylene at a higher uptake rate of comonomers, i.e., ethylene and α-olefin, manufacture of a rubber component having a higher molecular weight, and manufacture of homopolypropylene having a higher melting point through homopolymerization of propylene, compared to traditional metallocene catalysts, and also to provide a method of olefin polymerization in the presence of such a metallocene complex.

Solution to Problem

To solve the foregoing problems, the inventors have conducted various studies on metallocene polymerization catalysts. Specifically, the inventors have made research in various aspects and experimentally explored the ligand structure of transition metal compounds serving as metallocene complexes to complete a technique for providing (i) a higher ethylene or α-olefin uptake rate and (ii) a higher molecular weight and to produce (iii) homopolypropylene having a high melting point through highly stereospecific polymerization of propylene monomer in the homopolymerization of propylene, taking into account empirical rules on the symmetry attributed to the basic backbone, the mechanism of polymerization at catalytically active sites, and the influence of the steric and electronic effects of substituents on the coordinated monomer molecules and the growing polymer chains. After the research, the inventors have found that a transition metal compound having a particular steric structure provides high compatibility among the above three catalytic functions, and have completed the present invention.

That is, to solve the foregoing problems, the inventors have found a metallocene complex having particular substituents, particularly a metallocene complex having a substituent at position 6 of one or each indenyl ring and an optionally substituted furyl or thienyl group at position 2 of one or each indenyl ring, and have completed the invention from these findings.

Specifically, a first aspect of the present invention provides a metallocene complex represented by general formula [I]:

[Chem. 1]

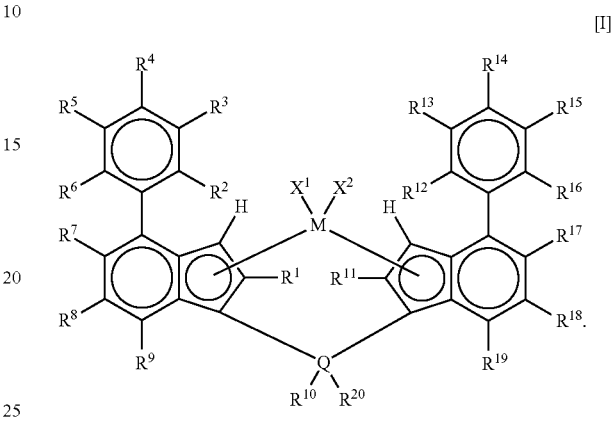

where M is titanium, zirconium, or hafnium; Q is carbon, silicon, or germanium; $X^1$ and $X^2$ are each independently a halogen atom, an alkyl group of 1 to 6 carbon atoms, an aryl group of 6 to 18 carbon atoms, an amino group substituted by an alkyl group of 1 to 6 carbon atoms, an alkoxy group of 1 to 6 carbon atoms, a halogenated alkyl group of 1 to 6 carbon atoms, or an halogenated aryl group of 6 to 18 carbon atoms; $R^1$ and $R^{11}$ may be the same or different and are each a hydrogen atom, an alkyl group of 1 to 6 carbon atoms, an alkoxy group of 1 to 6 carbon atoms, a furyl group, a thienyl group, a substituted furyl group, or a substituted thienyl group, at least one of $R^1$ and $R^{11}$ being necessarily a furyl group, a thienyl group, a substituted furyl group, or a substituted thienyl group; $R^8$ and $R^{18}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, an alkyl group of 1 to 6 carbon atoms having a trialkylsilyl group, a silyl group having a hydrocarbyl group of 1 to 6 carbon atoms, an aryl group of 6 to 18 carbon atoms, or a halogenated aryl group of 6 to 18 carbon atoms, where if either one of $R^8$ and $R^{18}$ is a hydrogen atom, the other one is not a hydrogen atom; $R^2$, $R^3$, $R^4$, $R^5$, $R^6$, $R^7$, $R^9$, $R^{12}$, $R^{13}$, $R^{14}$, $R^{15}$, $R^{16}$, $R^{17}$, and $R^{19}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, an alkyl group of 1 to 6 carbon atoms having a trialkylsilyl group, an aryl group of 6 to 18 carbon atoms, a halogenated aryl group of 6 to 18 carbon atoms, a furyl group, a thienyl group, a substituted furyl group, or a substituted thienyl group, any adjacent two of $R^2$, $R^3$, $R^4$, $R^5$, $R^6$, $R^{12}$, $R^{13}$, $R^{14}$, $R^{15}$, and $R^{16}$ optionally forming a 5- to 7-membered ring, the 5- to 7-membered ring optionally containing an unsaturated bond; and $R^{10}$ and $R^{20}$ may be the same or different and are each an alkyl group of 1 to 6 carbon atoms, a halogenated alkyl group of 1 to 6 carbon atoms, an alkyl group of 1 to 6 carbon atoms having a trialkylsilyl group, a silyl group having a hydrocarbyl group of 1 to 6 carbon atoms, an aryl group of 6 to 18 carbon atoms, a halogenated aryl group of 6 to 18 carbon atoms, or an optionally substituted 5- or 6-membered heterocyclic group, $R^{10}$ and $R^{20}$ optionally forming a 4- to 7-membered ring, the 4- to 7-membered ring optionally containing an unsaturated bond.

A second aspect of the present invention provides the metallocene complex according to the first aspect, wherein $R^8$ and $R^{18}$ in general formula [I] may be the same or different and are each an alkyl group of 1 to 6 carbon atoms.

A third aspect of the present invention provides the metallocene complex according to the first aspect, wherein $R^7$ and $R^{17}$ in general formula [I] may be the same or different and are each an alkyl group of 1 to 6 carbon atoms.

A fourth aspect of the present invention provides the metallocene complex according to the first aspect, wherein $R^2$, $R^6$, $R^9$, $R^{12}$, $R^{16}$, and $R^{19}$ in general formula [I] are each a hydrogen atom.

A fifth aspect of the present invention provides the metallocene complex according to the first aspect, wherein general formula [I] is represented by general formula [II]:

[Chem. 2]

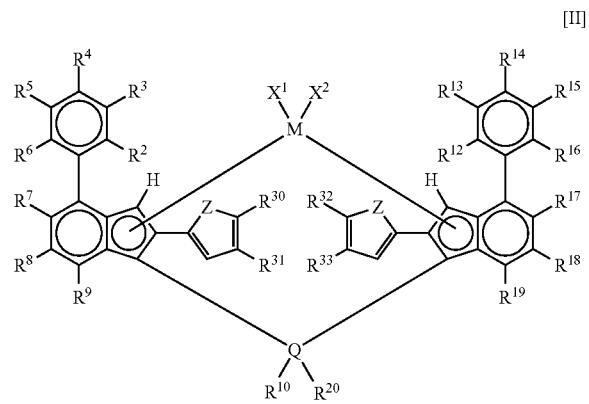

[II]

where Z is oxygen or sulfur; and $R^{30}$, $R^{31}$, $R^{32}$, and $R^{33}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, a silyl group having a hydrocarbyl group of 1 to 6 carbon atoms, or an aryl group of 6 to 18 carbon atoms, any adjacent two of $R^{30}$, $R^{31}$, $R^{32}$, and $R^{33}$ optionally forming a 5- to 7-membered ring, the 5- to 7-membered ring optionally containing an unsaturated bond.

A sixth aspect of the present invention provides an olefin polymerization catalyst containing the metallocene complex according to any one of the first to fifth aspects.

A seventh aspect of the present invention provides the olefin polymerization catalyst according to the sixth aspect, wherein the olefin polymerization catalyst contains the following components:

(A) the metallocene complex according to any one of the first to fifth aspects;

(B) a compound reactive with the component (A) to form an ion pair or an ion-exchangeable layered silicate; and (C) an organoaluminum compound.

An eighth aspect of the present invention provides the olefin polymerization catalyst according to the seventh aspect, wherein the component (B) is an ion-exchangeable layered silicate.

A ninth aspect of the present invention provides a method of olefin polymerization involving olefin polymerization or copolymerization in the presence of the olefin polymerization catalyst according to the seventh aspect.

A tenth aspect of the present invention provides a method for manufacturing a propylene-based polymer through two-step polymerization. This method includes the steps of, in the presence of the olefin polymerization catalyst according to the seventh aspect:

(i) polymerizing 90% to 100% by weight propylene and 0% to 10% by weight ethylene or α-olefin, based on the total weight of the monomer components; and (ii) polymerizing 10% to 90% by weight propylene and 10% to 90% by weight ethylene and/or α-olefin of 4 or more carbon atoms, based on the total weight of the monomer components.

An eleventh aspect of the present invention provides the method for manufacturing a propylene-based polymer through two-step polymerization according to the tenth aspect, wherein the first step involves (i) polymerizing 90% to 100% by weight propylene and 0% to 10% by weight ethylene or α-olefin, based on the total weight of the monomer components, by bulk polymerization in which propylene functions as a solvent or by gas-phase polymerization in which the monomers are maintained in gaseous form, and the second step involves (ii) polymerizing 10% to 90% by weight propylene and 10% to 90% by weight ethylene or α-olefin, based on the total weight of the monomer components, by gas-phase polymerization.

Advantageous Effects of Invention

A polymerization catalyst containing a metallocene complex according to the present invention has a higher uptake rate of ethylene or α-olefin, produces a rubber component, particularly an ethylene/propylene copolymer component, having a higher molecular weight, and facilitates manufacture of homopolypropylene having a higher melting point through homopolymerization of propylene, compared to traditional metallocene compounds.

This facilitates efficient manufacture of a propylene-based polymer having good flexibility and impact resistance and high rigidity. The novel metallocene complex and the novel method of olefin polymerization according to the present invention are significantly useful for industrial applications. For example, in the manufacture of a propylene/α-olefin block copolymer containing a polypropylene component and a propylene/α-olefin copolymer component by multi-step polymerization, a polypropylene component having high rigidity and a propylene/α-olefin copolymer component having a high α-olefin uptake rate and a high molecular weight can be simultaneously achieved to provide a propylene/α-olefin block copolymer having improved compatibility among rigidity and impact resistance.

The advantages of the present invention provided by the metallocene complex according to the present invention will now be discussed.

The metallocene complex of the present invention is a novel transition metal compound characterized by the electronic and steric structures of its ligands, which produce the catalytic functions of providing a high uptake rate of ethylene and α-olefin, facilitating manufacture of a rubber component having a high molecular weight, and producing homopolypropylene having a higher melting point through homopolymerization of propylene.

The metallocene complex is a transition metal compound having a structure represented by general formula [I] above.

In the present invention, the metallocene complex is used as a catalyst component of an olefin polymerization catalyst in combination with, for example, a co-catalyst to form an α-olefin polymerization catalyst.

As demonstrated by a comparison between the Examples and the Comparative Examples described later, an α-olefin polymerization metallocene catalyst containing the transition metal compound according to the present invention as an olefin polymerization catalyst component has a high uptake rate of ethylene and α-olefin, facilitates manufacture of a rubber component having a high molecular weight, and produces homopolypropylene having a higher melting point through homopolymerization of propylene.

Although the reason is not fully understood, it is believed that the uniqueness of the present invention is achieved by the unique structure of the transition metal compound represented by general formula [I] according to the present invention, which has an optionally substituted furyl or thienyl group at position 2 of one or each indenyl ring and a substituent at position 6 of one or each indenyl ring.

In particular, it is believed that the arrangement of a substituent at position 6 of one or each indenyl ring and an optionally substituted furyl or thienyl group at position 2 of one or each indenyl ring allows the furyl or thienyl group at position 2 of one or each indenyl ring to form a suitable dihedral angle with the indenyl ring so that the furyl or thienyl group produces the optimum steric effect on the coordination field.

As a result, the steric effect of the substituent at position 2 of the indenyl ring probably inhibits the polymer release reaction to increase the molecular weight of the resulting polymer and also allows selective propylene coordination in the propylene insertion reaction to produce the superior effect of allowing highly stereospecific polymerization.

The substituent at position 5 of the indenyl ring probably functions synergistically to provide a polymer having a high molecular weight.

As demonstrated by a comparison between the Examples and the Comparative Examples described later, in a structure having a hydrogen atom at position 5 of each indenyl ring, the substituent at position 4 of the indenyl ring cannot sufficiently inhibit the polymer release reaction. In a structure having an alkyl group at position 5 of one or each indenyl ring, the substituent at position 4 of the indenyl ring inhibits the polymer release reaction. This alkyl group, however, does not allow sufficient selective propylene coordination in the propylene insertion reaction, and there is still room for improvement in the melting point of homopolypropylene.

In contrast to these results, the structure achieved by the present invention, which has a substituent at position 6 of one or each indenyl ring and an optionally substituted furyl or thienyl group at position 2 of one or each indenyl ring, probably enables both the inhibition of the polymer release reaction and the selective propylene insertion reaction described above.

DESCRIPTION OF EMBODIMENTS

A metallocene complex and a method for manufacturing a propylene-based polymer in the presence of the metallocene complex (or metallocene compound) according to the present invention will now be described in detail for each item.

1. Metallocene Complex

The metallocene complex according to the present invention has particular substituents and is represented by general formula [I]:

[Chem. 3]

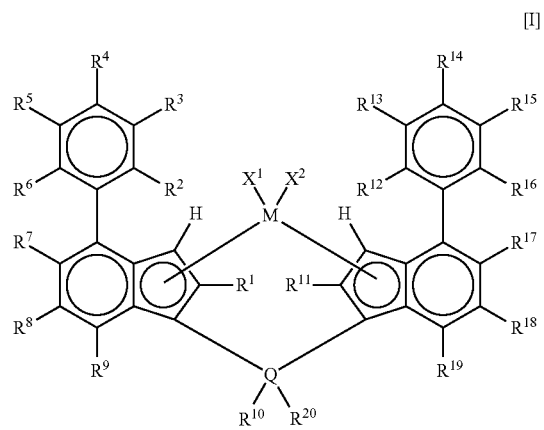

where M is titanium, zirconium, or hafnium; Q is carbon, silicon, or germanium; $X^1$ and $X^2$ are each independently a halogen atom, an alkyl group of 1 to 6 carbon atoms, an aryl group of 6 to 18 carbon atoms, an amino group substituted by an alkyl group of 1 to 6 carbon atoms, an alkoxy group of 1 to 6 carbon atoms, a halogenated alkyl group of 1 to 6 carbon atoms, or an halogenated aryl group of 6 to 18 carbon atoms; $R^1$ and $R^{11}$ may be the same or different and are each a hydrogen atom, an alkyl group of 1 to 6 carbon atoms, an alkoxy group of 1 to 6 carbon atoms, a furyl group, a thienyl group, a substituted furyl group, or a substituted thienyl group, at least one of $R^1$ and $R^{11}$ being necessarily a furyl group, a thienyl group, a substituted furyl group, or a substituted thienyl group; $R^8$ and $R^{18}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, an alkyl group of 1 to 6 carbon atoms having a trialkylsilyl group, a silyl group having a hydrocarbyl group of 1 to 6 carbon atoms, an aryl group of 6 to 18 carbon atoms, or a halogenated aryl group of 6 to 18 carbon atoms, where if either one of $R^8$ and $R^{18}$ is a hydrogen atom, the other one is not a hydrogen atom; $R^2$, $R^3$, $R^4$, $R^5$, $R^6$, $R^7$, $R^9$, $R^{12}$, $R^{13}$, $R^{14}$, $R^{15}$, $R^{16}$, $R^{17}$, and $R^{19}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, an alkyl group of 1 to 6 carbon atoms having a trialkylsilyl group, an aryl group of 6 to 18 carbon atoms, a halogenated aryl group of 6 to 18 carbon atoms, a furyl group, a thienyl group, a substituted furyl group, or a substituted $R^3$, $R^4$, $R^5$, $R^6$, $R^{12}$, $R^{13}$, $R^{14}$, $R^{15}$, and $R^{16}$ optionally forming a 5- to 7-membered ring, the thienyl group, any adjacent two of $R^2$, 5- to 7-membered ring optionally containing an unsaturated bond; and $R^{10}$ and $R^{20}$ may be the same or different and are each an alkyl group of 1 to 6 carbon atoms, a halogenated alkyl group of 1 to 6 carbon atoms, an alkyl group of 1 to 6 carbon atoms having a trialkylsilyl group, a silyl group having a hydrocarbyl group of 1 to 6 carbon atoms, an aryl group of 6 to 18 carbon atoms, a halogenated aryl group of 6 to 18 carbon atoms, or an optionally substituted 5- or 6-membered heterocyclic group, $R^{10}$ and $R^{20}$ optionally forming a 4- to 7-membered ring, the 4- to 7-membered ring optionally containing an unsaturated bond.

Examples of the alkyl groups of 1 to 6 carbon atoms in general formula [I] include methyl, ethyl, n-propyl, i-propyl, n-butyl, i-butyl, s-butyl, t-butyl, n-pentyl, n-hexyl, cyclopropyl, cyclopentyl, and cyclohexyl.

Examples of the alkoxy groups of 1 to 6 carbon atoms include methoxy, ethoxy, n-propoxy, i-propoxy, n-butoxy, i-butoxy, tert-butoxy, and phenoxy.

The aryl groups of 6 to 18 carbon atoms may be substituted by a hydrocarbyl group of 1 to 6 carbon atoms. Examples of the aryl groups of 6 to 18 carbon atoms include phenyl, tolyl, dimethylphenyl, ethylphenyl, trimethylphenyl, t-butylphenyl, biphenyl, 1-naphthyl, 2-naphthyl, acenaphthyl, phenanthryl, and anthryl.

Examples of the halogen atoms in general formula [I] include chlorine, bromine, iodine, and fluorine atoms. Examples of the alkenyl groups of 1 to 6 carbon atoms include vinyl, propenyl, allyl, butenyl, and cyclohexenyl. Examples of the amino groups substituted by an alkyl group of 1 to 6 carbon atoms include dimethylamino, diethylamino, di-n-propylamino, di-i-propylamino, and methylethylamino.

The halogenated alkyl groups of 1 to 6 carbon atoms are alkyl groups of 1 to 6 carbon atoms, their backbones being substituted by at least one halogen atom. Examples of the halogen atoms in the halogenated alkyl groups of 1 to 6 carbon atoms include fluorine, chlorine, bromine, and iodine atoms. Examples of the halogenated alkyl groups of 1 to 6 carbon atoms include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachioroethyl, pentafluoropropyl, nonafluorobutyl, 5-chloropentyl, 5,5,5-trichloropentyl, 5-fluoropentyl, 5,5,5-trifluoropentyl, 6-chlorohexyl, 6,6,6-trichlorohexyl, 6-fluorohexyl, and 6,6,6-trifluorohexyl.

In general formula [I], the silyl group having hydrocarbyl groups of 1 to 6 carbon atoms is a silyl substituent having three identical or different hydrocarbyl groups of 1 to 6 carbon atoms on the silicon atom. Examples of the hydrocarbyl groups of 1 to 6 carbon atoms include the alkyl groups of 1 to 6 carbon atoms, alkoxy groups of 1 to 6 carbon atoms, alkenyl groups of 1 to 6 carbon atoms, and halogenated alkyl groups of 1 to 6 carbon atoms in general formula [I], and also include phenyl, which may have a substituent. Examples of the silyl groups having hydrocarbyl groups of 1 to 6 carbon atoms include trimethylsilyl, triethylsilyl, tri-n-butylsilyl, t-butyldimethylsilyl, trivinylsilyl, triallylsilyl, and triphenylsilyl.

The halogenated aryl groups of 6 to 18 carbon atoms in general formula [I] are aryl groups of 6 to 18 carbon atoms substituted by at least one halogen atom. Examples of the halogenated aryl groups of 6 to 18 carbon atoms include 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2,4-difluorophenyl, 2,5-difluorophenyl 2,6-difluorophenyl, 3,5-difluorophenyl, 2,4-dichlorophenyl, 2,5-dichlorophenyl, 2,6-dichlorophenyl, 3,5-dichlorophenyl, 2,4,6-trifluorophenyl, 2,3,4-trifluorophenyl, 2,4,5-trifluorophenyl, 3,4,5-trifluorophenyl, 2,4,6-trichlorophenyl, 2,3,4-trichlorophenyl, 2,4,5-trichlorophenyl, 3,4,5-trichlorophenyl, pentafluorophenyl, pentachlorophenyl, 3,5-dimethyl-4-chlorophenyl, and 3,5-dichloro-4-biphenyl.

Examples of the furyl, thienyl, substituted furyl, and substituted thienyl groups in general formula [I] include 2-furyl, 2-(5-methylfuryl), 2-(5-ethylfuryl), 2-(5-n-propylfuryl), 2-(5-i-propylfuryl), 2-(5-t-butylfuryl), 2-(5-trimethylsilylfuryl), 2-(5-triethylsilylfuryl), 2-(5-phenylfuryl), 2-(5-tolylfuryl), 2-(5-fluorophenylfuryl), 2-(5-chlorophenylfuryl), 2-(4,5-dimethylfuryl), 2-(3,5-dimethylfuryl), 2-benzofuryl, 3-furyl, 3-(5-methylfuryl), 3-(5-ethylfuryl), 3-(5-n-propylfuryl), 3-(5-i-propylfuryl), 3-(5-t-butylfuryl), 3-(5-trimethylsilylfuryl), 3-(5-triethylsilylfuryl), 3-(5-phenylfuryl), 3-(5-tolylfuryl), 3-(5-fluorophenylfuryl), 3-(5-chlorophenylfuryl), 3-(4,5-dimethylfuryl), 3-benzofuryl, 2-thienyl, 2-(5-methylthienyl), 2-(5-ethylthienyl), 2-(5-n-propylthienyl), 2-(5-i-propylthienyl), 2-(5-t-butylthienyl), 2-(5-trimethylsilylthienyl), 2-(5-triethylsilylthienyl), 2-(5-phenylthienyl), 2-(5-tolylthienyl), 2-(5-fluorophenylthienyl), 2-(5-chlorophenylthienyl), 2-(4,5-dimethylthienyl), 2-(3,5-dimethylthienyl), 2-benzothienyl, 3-thienyl, 3-(5-methylthienyl), 3-(5-ethylthienyl), 3-(5-n-propylthienyl), 3-(5-i-propylthienyl), 3-(5-t-butylthienyl), 3-(5-trimethylsilylthienyl), 3-(5-triethylsilylthienyl), 3-(5-phenylthienyl), 3-(5-tolylthienyl), 3-(5-fluorophenylthienyl), 3-(5-chlorophenylthienyl), 3-(4,5-dimethylthienyl), and 3-benzothienyl.

The optionally substituted 5- or 6-membered heterocyclic groups in general formula [I] refer to groups having a heteroatom that does not form a direct bond with the alkadienyl group. Examples of the heterocycles include pyrrolidyl, pyridyl, pyrimidyl, quinolyl, isoquinolyl, carbazolyl, furyl, thienyl, thienofuryl, imidazolyl, pyrazolyl, pyrrolyl, oxazolyl, thiazolyl, isothiazolyl, and isooxazolyl. These heterocycles may be substituted by an alkyl group of 1 to 6 carbon atoms, an alkenyl group of 1 to 6 carbon atoms, a halogenated alkyl group of 1 to 6 carbon atoms, a silyl group having a hydrocarbyl group of 1 to 6 carbon atoms, an aryl group of 6 to 18 carbon atoms, or a halogenated aryl group of 6 to 18 carbon atoms. A 5- to 7-membered ring may be formed between any two adjacent atoms on the heterocycles. The 5- to 7-membered ring may contain an unsaturated bond. The 5- to 7-membered ring may contain a heteroatom. Examples of the 5- to 7-membered ring include furyl, thienyl, substituted furyl, and substituted thienyl groups, which are described above.

In general formula [I], M is titanium, zirconium, or hafnium, preferably zirconium or hafnium, more preferably zirconium; and Q is carbon, silicon, or germanium, preferably silicon or germanium. The substituents $R^{10}$ and $R^{20}$ on Q may form a 4- to 7-membered ring. Examples of such rings include silacyclobutane, silacyclopentane, 2,5-dimethylsilacyclopentane, silacyclohexane, and silafluorene.

$X^1$ and $X^2$ are each a ligand that forms a σ bond with M and are each independently a halogen atom, an alkyl group of 1 to 6 carbon atoms, an aryl group of 6 to 18 carbon atoms, a substituted amino group of 1 to 20 carbon atoms, an alkoxy group of 1 to 6 carbon atoms, a halogenated alkyl group of 1 to 6 carbon atoms, or a halogenated aryl group of 6 to 18 carbon atoms.

Among these groups, preferred are halogen atoms and hydrocarbyl groups of 1 to 6 carbon atoms, specifically, chlorine, bromine, iodine, methyl, ethyl, i-butyl, and phenyl.

$R^8$ and $R^{18}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, an alkyl group of 1 to 6 carbon atoms having a trialkylsilyl group, a silyl group having a hydrocarbyl group of 1 to 6 carbon atoms, an aryl group of 6 to 18 carbon atoms, or a halogenated aryl group of 6 to 18 carbon atoms. If either one of $R^8$ and $R^{18}$ is a hydrogen atom, the other one is not a hydrogen atom. Preferably, $R^8$ and $R^{18}$ are each an alkyl group of 1 to 6 carbon atoms or an alkoxy group of 1 to 6 carbon atoms, more preferably an alkyl group of 1 to 6 carbon atoms, even more preferably methyl.

$R^2$, $R^3$, $R^4$, $R^5$, $R^6$, $R^7$, $R^9$, $R^{12}$, $R^{13}$, $R^{14}$, $R^{15}$, $R^{16}$, $R^{17}$, and $R^{19}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, an alkyl group of 1 to 6 carbon atoms having a trialkylsilyl group, a silyl group having a hydrocarbyl group of 1 to 6 carbon atoms, an aryl group of 6 to 18 carbon atoms, a halogenated aryl group of 6 to 18 carbon atoms, a furyl group, a thienyl group, a substituted furyl group, or a substituted thienyl group.

$R^7$, $R^9$, $R^{17}$, and $R^{19}$, which are substituents on the indenyl groups, are each preferably a hydrogen atom, an alkyl group of 1 to 6 carbon atoms, or an alkoxy group of 1 to 6 carbon atoms. In particular, $R^7$ and $R^{17}$ are each preferably an alkyl group of 1 to 6 carbon atoms, more preferably methyl or ethyl, even more preferably methyl, and $R^9$ and $R^{19}$ are preferably a hydrogen atom.

$R^2$, $R^3$, $R^4$, $R^5$, $R^6$, $R^{12}$, $R^{13}$, $R^{19}$, $R^{15}$, and $R^{16}$, which are substituents on the phenyl groups at positions 4 of the indenyl groups, are each preferably a hydrogen atom, a halogen atom, an alkyl group of 1 to 6 carbon atoms, a silyl group having a hydrocarbyl group of 1 to 6 carbon atoms, or an aryl group of 6 to 18 carbon atoms.

Any adjacent two of $R^2$, $R^3$, $R^4$, $R^5$, $R^6$, $R^{12}$, $R^{13}$, $R^{14}$, $R^{15}$, and $R^{16}$ may form a 5- to 7-membered ring, and the 5- to 7-membered ring may contain an unsaturated bond.

Examples of the substituents at positions 4 of the indenyl groups include 1-naphthyl, 2-naphthyl, 5,6,7,8-tetrahydro-1-naphthyl, 5,6,7,8-tetrahydro-2-naphthyl, phenanthryl, and anthryl.

Of the substituents ($R^2$, $R^3$, $R^4$, $R^5$, $R^6$, $R^{12}$, $R^{13}$, $R^{14}$, $R^{15}$, and $R^{16}$) on the phenyl groups at positions 4 of the indenyl groups, at least one of $R^3$, $R^4$, $R^5$, $R^{13}$, $R^{14}$, $R^{15}$ and $R^{16}$ preferably has a substituent. More preferably, at least one of $R^3$, $R^4$, and $R^5$ and at least one of $R^{13}$, $R^{14}$, and $R^{15}$ preferably have a substituent.

Examples of preferred substituents include halogen atoms, alkyl groups of 1 to 6 carbon atoms, silyl groups having a hydrocarbyl group of 1 to 6 carbon atoms, and aryl groups of 6 to 18 carbon atoms.

$R^1$ and $R^{11}$, which are substituents at positions 2 of the indenyl rings, may be the same or different and are each a hydrogen atom, an alkyl group of 1 to 6 carbon atoms, an alkoxy group of 1 to 6 carbon atoms, a furyl group, a thienyl group, a substituted furyl group, or a substituted thienyl group. At least one of $R^1$ and $R^{11}$ should be necessarily a furyl group, a thienyl group, a substituted furyl group, or a substituted thienyl group.

Preferably, the substituents $R^1$ and $R^{11}$ are each an alkyl group of 1 to 6 carbon atoms, an optionally substituted furyl group, or a thienyl group. Examples of preferred alkyl groups of 1 to 6 carbon atoms include methyl, ethyl, n-propyl, n-butyl, i-propyl, and i-butyl, more preferably methyl.

Particularly preferred furyl, thienyl, substituted furyl, and substituted thienyl groups, among the substituents $R^1$ and $R^{11}$, can be represented by formula [III]:

[Chem. 4]

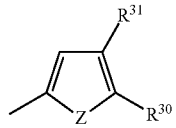

[III]

where Z is oxygen or sulfur; and $R^{30}$ and $R^{31}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, a silyl group having a hydrocarbyl group of 1 to 6 carbon atoms, or an aryl group of 6 to 18 carbon atoms. Adjacent $R^{31}$ and $R^{32}$ may form a 5- to 7-membered ring. The 5- to 7-membered ring may contain an unsaturated bond.

In general formula [III], the substituent $R^{31}$ is preferably a hydrogen atom, a halogen atom, an alkyl group of 1 to 6 carbon atoms, or an aryl group of 6 to 18 carbon atoms, more preferably a hydrogen atom or an alkyl group of 1 to 6 carbon atoms. The substituent $R^{30}$ is preferably a halogen atom, an alkyl group of 1 to 6 carbon atoms, or an aryl group of 6 to 18 carbon atoms, more preferably an alkyl group of 1 to 6 carbon atoms or an aryl group of 6 to 18 carbon atoms.

In general formula [I], $R^1$ and $R^{11}$ are each preferably a furyl group, a thienyl group, a substituted furyl group, or a substituted thienyl group. More preferably, $R^1$ and $R^{11}$ are each a substituted furyl group or a substituted thienyl group, even more preferably a substituted furyl group, which provides a high ethylene uptake rate.

In general formula [I], $R^4$ and $R^{14}$ preferably have substituents to provide high rubber polymerization activity. Examples of preferred substituents include halogen atoms, alkyl groups of 1 to 6 carbon atoms, alkoxy groups of 1 to 6 carbon atoms, halogenated alkyl groups of 1 to 6 carbon atoms, silyl groups having a hydrocarbyl group of 1 to 6 carbon atoms, aryl groups of 6 to 18 carbon atoms, and halogenated aryl groups of 6 to 18 carbon atoms, more preferably alkyl groups of 1 to 6 carbon atoms, halogenated alkyl groups of 1 to 6 carbon atoms, silyl groups having a hydrocarbyl group of 1 to 6 carbon atoms, and aryl groups of 6 to 18 carbon atoms.

Specifically, the metallocene complex according to the present invention has particular substituents and is represented by general formula [II]:

[Chem. 5]

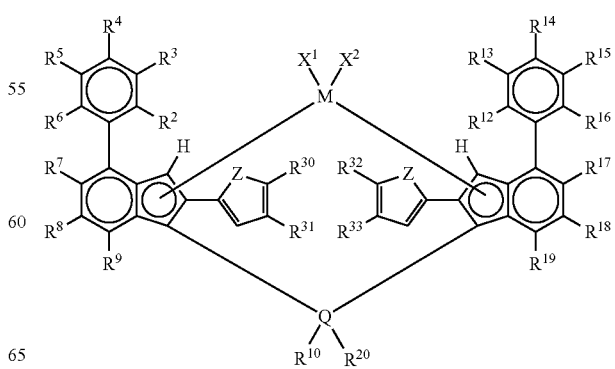

[II]

where Z is oxygen or sulfur; and $R^{30}$, $R^{31}$, $R^{32}$, and $R^{33}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, a silyl group having a hydrocarbyl group of 1 to 6 carbon atoms, or an aryl group of 6 to 18 carbon atoms. Any adjacent two of $R^{30}$, $R^{31}$, $R^{32}$, and $R^{33}$ may form a 5- to 7-membered ring, and the 5- to 7-membered ring may contain an unsaturated bond.

In general formula [II], M, $X^1$, $X^2$, Q, $R^2$, $R^3$, $R^4$, $R^5$, $R^6$, $R^7$, $R^8$, $R^9$, $R^{10}$, $R^{12}$, $R^{13}$, $R^{19}$, $R^{15}$, $R^{16}$, $R^{17}$, $R^{18}$, $R^{19}$, and $R^{20}$ are as defined in general formula [I]. The substituents $R^{31}$ and $R^{33}$ are each preferably a hydrogen atom, a halogen atom, an alkyl group of 1 to 6 carbon atoms, or an aryl group of 6 to 18 carbon atoms, more preferably a hydrogen atom or an alkyl group of 1 to 6 carbon atoms. The substituents $R^{30}$ and $R^{32}$ are each preferably a halogen atom, an alkyl group of 1 to 6 carbon atoms, or an aryl group of 6 to 18 carbon atoms, more preferably an alkyl group of 1 to 6 carbon atoms or an aryl group of 6 to 18 carbon atoms, even more preferably methyl.

Specific Examples of Metallocene Compounds

Specific examples of the metallocene complexes according to the present invention are listed below:
(1) Dimethylsilylene-bis[2-(2-furyl)-4-phenyl-6-methylindenyl]zirconium dichloride Metallocene Complexes Having Different Substituents at 4-Position of Each 5,6-Dimethylindenyl Backbone:
(2) Dimethylsilylene-bis[2-(5-methyl-2-furyl)-4-phenyl-5,6-dimethylindenyl]zirconium dichloride
(3) Dimethylsilylene-bis[2-(5-methyl-2-furyl)-4-(2-methylphenyl)-5,6-dimethylindenyl]zirconium dichloride
(4) Dimethylsilylene-bis[2-(5-methyl-2-furyl)-4-(2-ethylphenyl)-5,6-dimethylindenyl]zirconium dichloride
(5) Dimethylsilylene-bis[2-(5-methyl-2-furyl)-4-(2-methoxyphenyl)-5,6-dimethylindenyl]zirconium dichloride
(6) Dimethylsilylene-bis[2-(5-methyl-2-furyl)-4-(2-chlorophenyl)-5,6-dimethylindenyl]zirconium dichloride
(7) Dimethylsilylene-bis[2-(5-methyl-2-furyl)-4-(3-methylphenyl)-5,6-dimethylindenyl]zirconium dichloride
(8) Dimethylsilylene-bis[2-(5-methyl-2-furyl)-4-(3-methoxyphenyl)-5,6-dimethylindenyl]zirconium dichloride
(9) Dimethylsilylene-bis[2-(5-methyl-2-furyl)-4-(3-chlorophenyl)-5,6-dimethylindenyl]zirconium dichloride
(10) Dimethylsilylene-bis[2-(5-methyl-2-furyl)-4-(4-methylphenyl)-5,6-dimethylindenyl]zirconium dichloride
(11) Dimethylsilylene-bis[2-(5-methyl-2-furyl)-4-(4-ethylphenyl)-5,6-dimethylindenyl]zirconium dichloride
(12) Dimethylsilylene-bis[2-(5-methyl-2-furyl)-4-(4-i-propylphenyl)-5,6-dimethylindenyl]zirconium dichloride
(13) Dimethylsilylene-bis[2-(5-methyl-2-furyl)-4-(4-t-butylphenyl)-5,6-dimethylindenyl]zirconium dichloride
(14) Dimethylsilylene-bis[2-(5-methyl-2-furyl)-4-(4-biphenylyl)-5,6-dimethylindenyl]zirconium dichloride
(15) Dimethylsilylene-bis[2-(5-methyl-2-furyl)-4-(4-chlorophenyl)-5,6-dimethylindenyl]zirconium dichloride
(16) Dimethylsilylene-bis[2-(5-methyl-2-furyl)-4-(4-methoxyphenyl)-5,6-dimethylindenyl]zirconium dichloride
(17) Dimethylsilylene-bis[2-(5-methyl-2-furyl)-4-(4-trifluoromethylphenyl)-5,6-dimethylindenyl]zirconium dichloride
(18) Dimethylsilylene-bis[2-(5-methyl-2-furyl)-4-(4-trimethylsilylphenyl)-5,6-dimethylindenyl]zirconium dichloride
(19) Dimethylsilylene-bis[2-(5-methyl-2-furyl)-4-(3,5-dimethylphenyl)-5,6-dimethylindenyl]zirconium dichloride
(20) Dimethylsilylene-bis[2-(5-methyl-2-furyl)-4-(3,5-diethylphenyl)-5,6-dimethylindenyl]zirconium dichloride
(21) Dimethylsilylene-bis[2-(5-methyl-2-furyl)-4-(3,5-di-i-propylphenyl)-5,6-dimethylindenyl]zirconium dichloride
(22) Dimethylsilylene-bis[2-(5-methyl-2-furyl)-4-(3,5-di-t-butylphenyl)-5,6-dimethylindenyl]zirconium dichloride
(23) Dimethylsilylene-bis[2-(5-methyl-2-furyl)-4-(3,5-dimethoxyphenyl)-5,6-dimethylindenyl]zirconium dichloride
(24) Dimethylsilylene-bis[2-(5-methyl-2-furyl)-4-(3,5-ditrifluoromethylphenyl)-5,6-dimethylindenyl]zirconium dichloride
(25) Dimethylsilylene-bis[2-(5-methyl-2-furyl)-4-(3,4,5-trimethylphenyl)-5,6-dimethylindenyl]zirconium dichloride
(26) Dimethylsilylene-bis[2-(5-methyl-2-furyl)-4-(3,5-dimethyl-4-trimethylsilylphenyl)-5,6-dimethylindenyl]zirconium dichloride
(27) Dimethylsilylene-bis[2-(5-methyl-2-furyl)-4-(3,5-dichloro-4-trimethylsilylphenyl)-5,6-dimethylindenyl]zirconium dichloride
(28) Dimethylsilylene-bis[2-(5-methyl-2-furyl)-4-(1-naphthyl)-5,6-dimethylindenyl]zirconium dichloride
(29) Dimethylsilylene-bis[2-(5-methyl-2-furyl)-4-(2-naphthyl)-5,6-dimethylindenyl]zirconium dichloride
(30) Dimethylsilylene-bis[2-(5-methyl-2-furyl)-4-(9-phenanthryl-5,6-dimethylindenyl]zirconium dichloride
(31) Dimethylsilylene-bis[2-(5-methyl-2-furyl)-4-(2-phenanthryl)-5,6-dimethylindenyl]zirconium dichloride
Metallocene Complexes Having Different Substituents on Furyl or Thienyl Group at 2-Position of Each 5,6-Dimethylindenyl Backbone:
(32) Dimethylsilylene-bis[2-(5-trimethylsilyl-2-furyl)-4-phenyl-5,6-dimethylindenyl]zirconium dichloride
(33) Dimethylsilylene-bis[2-(5-phenyl-2-furyl)-4-phenyl-5,6-dimethylindenyl]zirconium dichloride
(34) Dimethylsilylene-bis[2-(4,5-dimethyl-2-furyl)-4-phenyl-5,6-dimethylindenyl]zirconium dichloride
(35) Dimethylsilylene-bis[2-(4,5-benzo-2-furyl)-4-phenyl-5,6-dimethylindenyl]zirconium dichloride
(36) Dimethylsilylene-bis[2-(5-methyl-2-thienyl)-4-phenyl-5,6-dimethylindenyl]zirconium dichloride
(37) Dimethylsilylene-bis[2-(5-trimethylsilyl-2-furyl)-4-(3,5-dimethylphenyl)-5,6-dimethylindenyl]zirconium dichloride
(38) Dimethylsilylene-bis[2-(5-phenyl-2-furyl)-4-(3,5-dimethylphenyl)-5,6-dimethylindenyl]zirconium dichloride
(39) Dimethylsilylene-bis[2-(4,5-dimethyl-2-furyl)-4-(3,5-dimeth ylphenyl)-5,6-dimethylindenyl]zirconium dichloride
(40) Dimethylsilylene-bis[2-(4,5-benzofuryl-2-furyl)-4-(3,5-dimethylphenyl)-5,6-dimethylindenyl]zirconium dichloride
(41) Dimethylsilylene-bis[2-(5-methyl-2-thienyl)-4-(3,5-dimethylphenyl)-5,6-dimethylindenyl]zirconium dichloride
(42) Dimethylsilylene-bis[2-(5-trimethylsilyl-2-furyl)-4-(4-t-butylphenyl)-5,6-dimethylindenyl]zirconium dichloride
(43) Dimethylsilylene-bis[2-(5-phenyl-2-furyl)-4-(4-t-butylphenyl)-5,6-dimethylindenyl]zirconium dichloride
(44) Dimethylsilylene-bis[2-(4,5-dimethyl-2-furyl)-4-(4-t-butylphenyl)-5,6-dimethylindenyl]zirconium dichloride
(45) Dimethylsilylene-bis[2-(4,5-benzofuryl-2-furyl)-4-(4-t-butylphenyl)-5,6-dimethylindenyl]zirconium dichloride
(46) Dimethylsilylene-bis[2-(5-methyl-2-thienyl)-4-(4-t-butylphenyl)-5,6-dimethylindenyl]zirconium dichloride Metallocene Complexes Having Asymmetric Substituents at 2-Positions of 5,6-Dimethylindenyl Backbones:

(47) Dimethylsilylene[4-phenyl-5,6-dimethylindenyl][2-(5-methyl-2-furyl)-4-phenyl-5,6-dimethylindenyl]zirconium dichloride
(48) Dimethylsilylene[2-methyl-4-phenyl-5,6-dimethylindenyl][2-(5-methyl-2-furyl)-4-phenyl-5,6-dimethylindenyl]zirconium dichloride
(49) Dimethylsilylene[2-ethyl-4-phenyl-5,6-dimethylindenyl][2-(5-methyl-2-furyl)-4-phenyl-5,6-dimethylindenyl]zirconium dichloride
(50) Dimethylsilylene[2-(5-methyl-2-furyl)-4-phenyl-5,6-dimethylindenyl][2-(5-ethyl-2-furyl)-4-phenyl-5,6-dimethylindenyl]zirconium dichloride
(51) Dimethylsilylene[2-(5-methyl-2-furyl)-4-phenyl-5,6-dimethylindenyl][2-(5-trimethylsilyl-2-furyl)-4-phenyl-5,6-dimethylindenyl]zirconium dichloride
(52) Dimethylsilylene[2-(5-methyl-2-furyl)-4-phenyl-5,6-dimethylindenyl][2-(5-methyl-2-thienyl)-4-phenyl-5,6-dimethylindenyl]zirconium dichloride Metallocene Complexes Having Different Substituents at 5- and 6-Positions of Each 5,6-Dimethylindenyl Backbone:

(53) Dimethylsilylene-bis[2-(5-methyl-2-furyl)-4-phenyl-5-methyl-6-ethylindenyl]zirconium dichloride
(54) Dimethylsilylene-bis[2-(5-methyl-2-furyl)-4-phenyl-5-methyl-6-i-propylindenyl]zirconium dichloride
(55) Dimethylsilylene-bis[2-(5-methyl-2-furyl)-4-phenyl-5-methyl-6-n-propylindenyl]zirconium dichloride
(56) Dimethylsilylene-bis[2-(5-methyl-2-furyl)-4-phenyl-5-ethyl-6-methylindenyl]zirconium dichloride
(57) Dimethylsilylene-bis[2-(5-methyl-2-furyl)-4-phenyl-5-n-propyl-6-methylindenyl]zirconium dichloride
(58) Dimethylsilylene-bis[2-(5-methyl-2-furyl)-4-phenyl-5-i-propyl-6-methylindenyl]zirconium dichloride Other examples include compounds of which the central metal M is hafnium in place of zirconium in the compounds listed above, compounds of which the crosslink $R^{10}QR^{11}$ is diethylsilylene, diphenylsilylene, dimethylgermylene, diethylgermylene, or diphenylgermylene in place of dimethylsilylene in the compounds listed above, and compounds of which at least one of $X^1$ and $X^2$ is a functional group, such as bromine, iodine, methyl, phenyl, dimethylamino, or diethylamino, in place of chlorine in the compounds listed above.

Synthesis of Metallocene Compound

The metallocene complex (compound) according to the present invention can be synthesized by any method depending on the types of substituents and bonds. A typical synthetic route is illustrated below.

[Chem. 6]

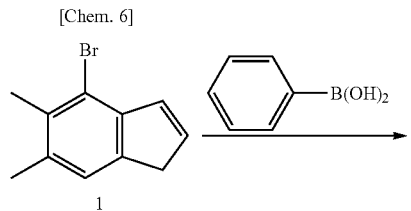

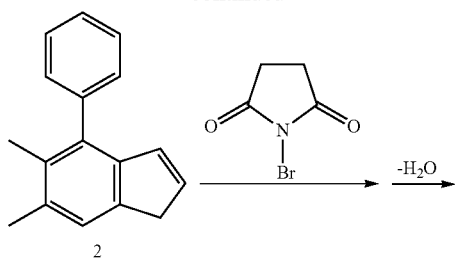

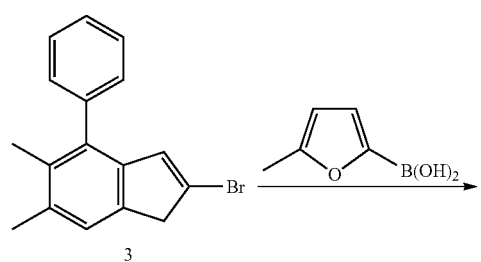

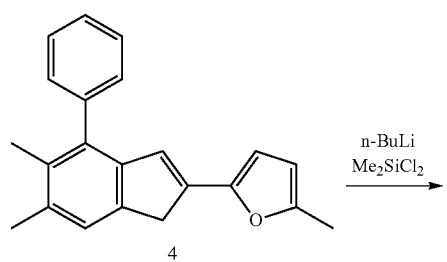

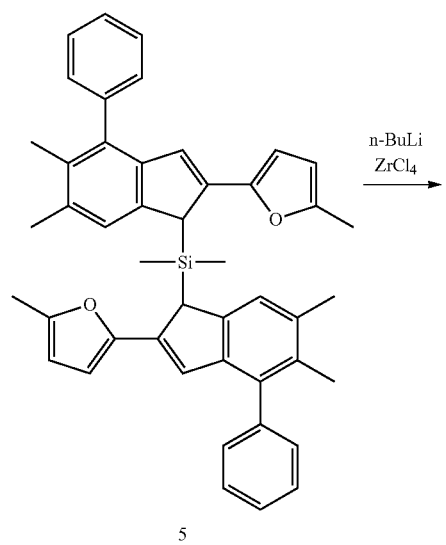

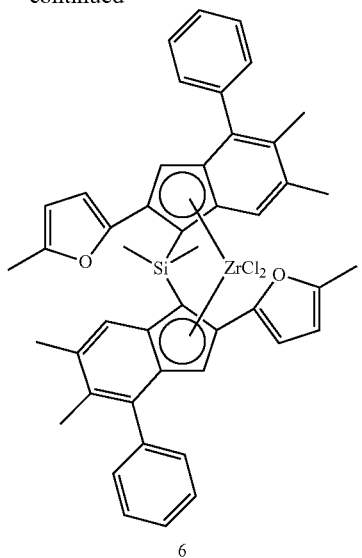

6

In the synthetic route, Compound 1 is coupled with phenylboronic acid in the presence of a palladium catalyst to form Compound 2. Compound 2 can be brominated into Compound 3 by a process disclosed in literature, for example, J. Org. Chem. 1982, 47, 705-709. Specifically, Compound 2 can be reacted with N-bromosuccinimide in the presence of water and dehydrated with an acid, such as p-toluenesulfonic acid. Compound 3 is coupled with 5-methylfuryl-2-boronic acid in the presence of a palladium catalyst to form Compound 4. Compound 4 is anionized with, for example, butyllithium and then reacted with dimethyldichlorosilane to form Crosslinked Compound 5. Compound 5 is converted into a dianion with 2 equivalents of n-butyllithium, for example, and then reacted with zirconium tetrachloride to form Metallocene Compound 6.

A substituted metallocene compound can be synthesized from the corresponding substituted raw material. For example, 5-methylfuryl-2-boronic acid may be replaced with other substituted boronic acids, such as 4,5-dimethylfuryl-2-boronic acid and 2-thienylboronic acid, to introduce the corresponding 2-substituents ($R^1$ and $R^{11}$). To introduce 2-alkyl substituents ($R^1$ and $R^{11}$), Compound 3 may be reacted with a Grignard reagent in the presence of a nickel catalyst, as disclosed in literature, for example, J. Org. Chem. 1984, 49, 4226.

A metallocene compound having different substituents on the two indenyl rings can be synthesized by sequentially reacting different substituted indenes with $Me_2QCl_2$ to crosslink the indenes. During crosslinking, crosslinking aids such as amines (e.g., methylimidazole) may be present.

2. Olefin Polymerization Catalyst

The metallocene complex according to the present invention can be used as one component of an olefin polymerization catalyst. In other words, the olefin polymerization catalyst preferably contains the metallocene complex as a component (A), as described below.

(1) Components of Olefin Polymerization Catalyst

The olefin polymerization catalyst according to the present invention contains the following components:

(A) a metallocene complex represented by general formula [I] or [II];

(B) a compound reactive with the component (A) to form an ion pair or an ion-exchangeable layered silicate; and (C) an organoaluminum compound.

(2) Individual Components

The component (A) may be a single metallocene complex represented by general formula [I] or [II] or may be two or more different metallocene complexes represented by general formula [I] or [II].

Examples of the component (B), i.e., the compound reactive with the component (A) to form an ion pair or an ion-exchangeable layered silicate, include aluminumoxy compounds, boron compounds, and ion-exchangeable layered silicates, preferably ion-exchangeable layered silicates. These components (B) may be used alone or in combination.

Aluminumoxy compounds can activate metallocene complexes. Examples of such compounds are represented by the following general formulae:

[Chem. 7]

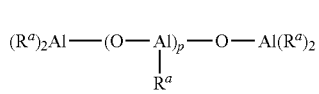 [IV]

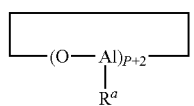 [V]

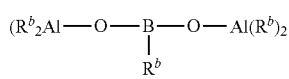 [VI]

where $R^a$ is a hydrogen atom or a hydrocarbyl group, preferably a hydrocarbyl group of 1 to 10 carbon atoms, even more preferably a hydrocarbyl group of 1 to 6 carbon atoms; each $R^a$ may be the same or different; and p is an integer of 0 to 40, preferably 2 to 30.

Compounds represented by general formulae [IV] and [V] are termed aluminoxanes. Preferred examples of the aluminoxanes include methylaluminoxane and methylisobutylaluminoxane. These aluminoxanes may be used in combination in the same group or different groups. These aluminoxanes can be prepared under any known conditions.

A compound represented by general formula [VI] can be prepared by reacting at least one trialkylaluminum with an alkylboronic acid represented by the general formula $R^bB(OH)_2$ in a molar ratio of 10:1 to 1:1, where $R^b$ is a hydrocarbyl group of 1 to 10 carbon atoms, preferably a hydrocarbyl group of 1 to 6 carbon atoms.

Examples of the boron compounds include complexes of cations, such as carbonium and ammonium cations, with organoboron compounds, such as triphenylboron, tris(3,5-difluorophenyl)boron, and tris(pentafluorophenyl)boron; and miscellaneous organoboron compounds, such as tris(pentafluorophenyl)boron.

Ion-exchangeable layered silicates (which may hereinafter be referred to simply as "silicates") have a crystal structure consisting of planes that are formed by bonds such as ionic bonds and are stacked in parallel on top of each other by binding force, where the ions present therein are exchangeable. Various silicates are known, as are listed in Haruo Shirozu, "Nendo Kobutsu Gaku (Clay Mineralogy)", Asakura Publishing Co., Ltd. (1995).

Examples of components (B) suitable for use in the present invention include those belonging to the smectite group, such as montmorillonite, sauconite, beidellite, nontronite, saponite, hectorite, and stevensite. In particular, montmorillonite is preferred in view of the rubber polymerization activity and the molecular weight of the rubber component.

Most natural silicates occur mainly in the form of the major components of clay minerals and often contain impurities (e.g., quartz and cristobalite) other than ion-exchangeable layered silicates. The smectite silicates used in the present invention may contain impurities other than ion-exchangeable layered silicates.

Granulation of Ion-Exchangeable Layered Silicate

The silicate may be used in a dry or slurried state. The ion-exchangeable layered silicate may have any shape, such as the shape of naturally occurring silicate or the shape of as-synthesized silicate. Alternatively, ion-exchangeable layered silicates having shapes adjusted by operations, such as pulverization, granulation, and sizing, may be used. Particularly preferred are granulated silicates, which give good polymer particulate characteristics.

The shape of the ion-exchangeable layered silicate may be adjusted by operations such as granulation, pulverization, and sizing before or after acid treatment.

Examples of granulation processes used herein include, but not limited to, stirring granulation, spray granulation, tumbling granulation, briquetting, compacting, extrusion granulation, fluidized bed granulation, emulsification granulation, submerged granulation, and compression molding granulation, preferably stirring granulation, spray granulation, tumbling granulation, and fluidized bed granulation, even more preferably stirring granulation and spray granulation.

In spray granulation, the dispersion medium used for the raw material slurry is water or an organic solvent such as methanol, ethanol, chloroform, methylene chloride, pentane, hexane, heptane, toluene, or xylene, preferably water. The concentration of the component (B) in the raw material slurry at which spherical particles form during spray granulation is 0.1% to 30% by weight, preferably 0.5% to 20% by weight, more preferably 1% to 10% by weight. The inlet temperature of hot air at which spherical particles form during spray granulation depends on the dispersion medium. For example, if water is used, the inlet temperature is 80° C. to 260° C., preferably 100° C. to 220° C.

In granulation, the silicate is optionally pulverized to form carrier particles with high strength and to improve the propylene polymerization activity. The silicate may be pulverized by any process. Examples of pulverization processes include both dry pulverization processes and wet pulverization processes. Preferred pulverization processes are wet pulverization processes using water as the dispersion medium, which are based on the swelling of the silicate. The pulverization may be performed by forced stirring, for example, with a Polytron homogenizer, or with a Dyno-Mill or a pearl mill. The average particle size before granulation is 0.01 to 3 µm, preferably 0.05 to 1 µm.

The granulation may be performed with a variety of binders of organic materials, inorganic solvents, and/or inorganic salts. Specific examples of such binders include magnesium chloride, aluminum sulfate, aluminum chloride, magnesium sulfate, alcohols, and glycols.

The prepared spherical particles preferably have a compressive fracture strength of 0.2 MPa or more so as not to be broken or powdered during the polymerization process. The granulated ion-exchangeable layered silicate has a particle size of 0.1 to 1,000 µm, preferably 1 to 500 µm. Any pulverization process may be used, including dry pulverization processes and wet pulverization processes.

Acid Treatment

The silicate used in the present invention is subjected to acid treatment before use. The acid treatment may be combined with other chemical treatments. Examples of other chemical treatments include alkali treatment, salt treatment, and organic treatment.

The acid treatment of the silicate alters the acidity of the solid. The acid treatment is not only effective in ion exchange and removal of surface impurities, but is also effective in partial dissolution of anions, such as aluminum, iron, magnesium, and lithium ions, from the crystalline structure.

Examples of the acids used in acid treatment include hydrochloric acid, nitric acid, sulfuric acid, phosphoric acid, acetic acid, oxalic acid, benzoic acid, stearic acid, propionic acid, acrylic acid, maleic acid, fumaric acid, and phthalic acid. Two or more of these acids may be used in combination. Particularly preferred are inorganic acids, more preferably sulfuric acid, hydrochloric acid, and nitric acid, even more preferably sulfuric acid.

Particularly preferred methods are combinations of acid treatment and salt treatment, for example, acid treatment after salt treatment, salt treatment after acid treatment, simultaneous acid and salt treatment, and simultaneous salt and acid treatment after salt treatment.

The acid treatment is preferably performed under conditions involving at least partial dissolution of the compound to be treated, typically at an acid content of 0.1% to 30% by weight and a temperature of room temperature to the boiling point of the solvent for 5 minutes to 24 hours. The acid is typically used in the form of an aqueous solution. For example, if sulfuric acid is used, the acid treatment is preferably performed at a temperature of 80° C. to 100° C. for 0.5 hour to less than 5 hours.

Simultaneous salt and acid treatment forms, for example, an ionic complex, molecular complex, or organic derivative and thus changes the surface area or the interlayer distance. For example, the interlayer distance of the layered substance can be increased based on its ion exchange ability, i.e., by replacing interlayer exchangeable ions with other bulky ions.

The shape may be controlled before, during, or after the acid treatment by pulverization and/or granulation. The acid treatment may be used in combination with any other chemical treatment, for example, alkali treatment, organic compound treatment, or organometallic treatment.

The salt used for ion exchange is a compound composed of a cation of at least one atom selected from the group consisting of group 1 to 14 atoms, preferably a compound composed of a cation of at least one atom selected from the group consisting of group 1 to 14 atoms and an anion derived from at least one atom or atomic group selected from the group consisting of halogen atoms, inorganic acids, and organic acids, even more preferably a compound composed of a cation of at least one atom selected from the group consisting of group 2 to 14 atoms and at least one anion selected from the group consisting of Cl, Br, I, F, $PO_4$, $SO_4$, $NO_3$, $CO_3$, $C_2O_4$, $ClO_3$, $ClO_4$, $OOCCH_3$, $CH_3COCHCOCH_3$, $OCl_2$, $O(NO_3)_2$, $O(ClO_4)_2$, $O(SO_4)$, OH, $O_2Cl_2$, $OCl_3$, OOCH, $OOCCH_2CH_3$, $C_2H_4O_4$, and $C_6H_5O_7$. Two or more among these salts may be used in combination.

The resulting silicate preferably has a volume of pores with radii of 20 Å or more of 0.1 $cm^3/g$ or more, more preferably 0.3 to 5 $cm^3/g$, as measured by a mercury intrusion method. The silicate contains adsorbed water and interlayer water after treatment in an aqueous solution. As used herein, the term "adsorbed water" refers to water adsorbed onto the surfaces or the fractured faces of the silicate crystal, and the term "interlayer water" refers to water present between crystal layers.

The adsorbed water and the interlayer water are preferably removed from the silicate before use. The silicate may be dehydrated by any method, such as thermal dehydration, thermal dehydration under a gas stream, thermal dehydration under reduced pressure, or azeotropic dehydration with organic solvents. The heating temperature is within a range where no adsorbed water or interlayer water remains, typically 100° C. or higher, preferably 150° C. or higher, although elevated temperatures causing structural disorder are not preferred. The heating time is 0.5 hour or more, preferably 1 hour or more. The weight loss of the silicate after dehydration drying is preferably 3% or less as measured after suction at a temperature of 200° C. and a pressure of 1 mmHg for 2 hours. If a silicate after a weight loss of 3% or less is used in the present invention, the silicate is preferably handled in such a way that the same weight loss is maintained when the silicate is put into contacted with the components (A) and (C).

Composition of Silicate after Acid Treatment

The acid-treated silicate, which is the component (B) in the present invention, preferably has an atomic ratio of aluminum to silicon of 0.01 to 0.29, more preferably 0.03 to 0.25, even more preferably 0.05 to 0.23, in view of the activity of the polymerization catalyst and the molecular weight of the rubber component.

The atomic ratio of aluminum to silicon, serving as a measure of the degree of acid treatment in the clay portion, can be controlled depending on the type of acid used for acid treatment, the acid content, the acid treating time, and the temperature.

The aluminum and silicon contents of the silicate are determined by X-ray fluorescence with a calibration curve prepared by chemical analysis in accordance with JIS.

Component (C)

An example organoaluminum compound is represented by the following general formula:

where R is a hydrocarbyl group of 1 to 20 carbon atoms, X is a hydrogen atom, a halogen atom, an alkoxy group, or a siloxy group, and a is a number of more than 0 to 3.

Examples of the organoaluminum compounds represented by the general formula include trialkylaluminums, such as trimethylaluminum, triethylaluminum, tripropylaluminum, and triisobutylaluminum; and halogenated or alkoxylated alkylaluminums, such as diethylaluminum monochloride and diethylaluminum monomethoxide. Particularly preferred are trialkylaluminums. These organoaluminum compounds may be used in combination.

(3) Preparation of Catalyst

In a method for preparing the olefin polymerization catalyst according to the present invention, the components (A), (B), and (C) may be put into contact with each other in any manner, for example, by the following processes:

(i) contact of the component (A) with the component (B) before addition of the component (C);

(ii) contact of the component (A) with the component (C) before addition of the component (B);

(iii) contact of the component (B) with the component (C) before addition of the component (A); and (iv) simultaneous contact of the components (A), (B), and (C) with each other.

Each component may be a mixture of different compounds. These compounds may be separately put into contact indifferent orders. Each component may be put into contact with each other during the preparation of the catalyst, during olefin prepolymerization, or during olefin polymerization.

Each component may be put into contact with each other in portions. For example, the components (B) and (C) may be put into contact with each other before addition of a mixture of the components (A) and (C).

The compounds (A), (B), and (C) are preferably put into contact with each other in an inert hydrocarbon solvent, such as pentane, hexane, heptane, toluene, or xylene, in an inert gas, such as nitrogen. The compounds (A), (B), and (C) may be put into contact with each other at a temperature of −20° C. to the boiling point of the solvent, preferably at a temperature of room temperature to the boiling point of the solvent.

If the component (B) in the polymerization catalyst according to the present invention is a silicate, the component (A), which is a metallocene compound, is preferably used in an amount of 0.001 to 10 mmol, more preferably 0.001 to 1 mmol, per gram of the component (B). The component (C) is preferably used in an amount corresponding to a molar ratio of aluminum to metallocene compound of 0.1 to 100,000, more preferably 1 to 10,000. These proportions are illustrative only and should not be intended to limit the present invention provided that the catalyst conforms to the object of the present invention.

Prior to the use of the catalyst containing the components (A), (B), and (C) in olefin polymerization (main polymerization), olefins such as ethylene, propylene, 1-butene, 1-hexene, 1-octene, 4-methyl-1-pentene, 3-methyl-1-butene, vinylcycloalkanes, and styrene may optionally be prepolymerized in small amounts. The prepolymerization may be performed by any known method.

(4) Olefin

The olefin polymerization catalyst according to the present invention can be used for homopolymerization of a single polymerizable monomer or copolymerization of two or more polymerizable monomers selected from the group consisting of ethylene and α-olefins.

The term "α-olefin" refers to, for example, olefins of 3 to 20 carbon atoms, including propylene, 1-butene, 1-pentene, 1-hexene, 1-heptene, 1-octene, 1-decene, 1-dodecene, 1-hexadecene, 4-methyl-1-pentene, styrene, vinylcyclohexane, dienes, trienes, and cyclic olefins.

3. Method of Polymerization

In the present invention, polymerization may be performed in any manner that allows the polymerization catalyst containing a metallocene complex represented by general formula [I] or [II] to contact efficiently with monomers to catalyze olefin polymerization or copolymerization.

Examples of methods usable in polymerization include slurry polymerization using inert solvents, bulk polymerization of propylene also functioning as a solvent substantially with use of no inert solvent, and gas-phase polymerization of gaseous monomers substantially with use of no liquid solvent.

Also applicable are continuous polymerization, batch polymerization, and prepolymerization.

Different types of polymerization may be used in any combination, including two-step bulk polymerization, bulk polymerization followed by gas-phase polymerization, and two-step gas-phase polymerization. A larger number of polymerization steps may be employed in the production of the polymer.

To form a polymer with a particularly good particle shape, it is preferred to perform the first step by bulk polymerization and the second step by gas-phase polymerization or to perform both the first and second steps by gas-phase polymerization.

The catalyst according to the present invention facilitates manufacture of a copolymer with a high molecular weight and manufacture of a propylene-based polymer with high rigidity and high impact resistance. Such a polymer is preferably manufactured by a method of polymerization including Steps 1 and 2 described below, more preferably a method of polymerization including Step 1 and then Step 2. These methods may be used in combination with other polymerization conditions to perform multistep polymerization including three or more steps.

Step 1

Step 1 involves polymerizing 90% to 100% by weight propylene and 0% to 10% by weight ethylene or α-olefin, based on the total weight of the monomer components.

For slurry polymerization, the polymerization solvent used is a saturated aliphatic or aromatic hydrocarbon, such as hexane, heptane, pentane, cyclohexane, benzene, toluene, or a mixture thereof.

The polymerization temperature is 0° C. to 150° C. Optionally, hydrogen can be used as a molecular weight modifier. A suitable polymerization pressure is 0 to 3 MPaG, preferably 0 to 2 MPaG.

For bulk polymerization, the polymerization temperature is 0° C. to 90° C., preferably 60° C. to 80° C. A suitable polymerization pressure is 0 to 5 MPaG, preferably 0 to 4 MPaG.

For gas-phase polymerization, the polymerization temperature is 0° C. to 200° C., preferably 50° C. to 120° C., more preferably 60° C. to 100° C. A suitable polymerization pressure is 0 to 4 MPaG, preferably 0 to 3 MPaG.

Ethylene and α-olefin may coexist in a total amount of 0% to 10% (not causing poor shaping of the polymer) of all monomer components to control the molecular weight, the activity, and the melting point. Hydrogen can be used as a molecular weight modifier.

Step 2

Step 2 involves polymerizing 10% to 90% by weight propylene and 10% to 90% by weight ethylene or α-olefin, based on the total weight of the monomer components, thereby producing a rubber component with suitable impact resistance. Preferably, propylene is present in an amount of 20% to 80% by weight based on the total weight of the monomer components, which gives a propylene polymer with high impact resistance.

For slurry polymerization and bulk polymerization, the polymerization conditions in the second step are the same as those in the first step. For gas-phase polymerization, which is performed in a monomer composition differing from that in the first step, the polymerization temperature is 0° C. to 200° C., preferably 20° C. to 90° C., more preferably 30° C. to 80° C. A suitable polymerization pressure is 0 to 4 MPaG, preferably 1 to 3 MPaG. Hydrogen can be used as a molecular weight modifier.

If ethylene is used as a monomer in Step 2, the propylene-based polymer prepared by the method of polymerization according to the present invention has an ethylene-containing fraction, which is observed in a fraction soluble at 100° C. in CFC (cross-fractionation chromatography)-IR. The ethylene-containing fraction probably improves the impact resistance and the transparency.

Polymerizable Monomer

In the present invention, as described above, the term "α-olefin" refers to olefins of 3 to 20 carbon atoms, including propylene, 1-butene, 1-pentene, 1-hexene, 1-heptene, 1-octene, 1-decene, 1-dodecene, 1-hexadecene, 4-methyl-1-pentene, styrene, vinylcyclohexane, dienes, trienes, and cyclic olefins.

Preferred examples of monomers used in combination with propylene include ethylene and 1-butene, more preferably ethylene. These monomers may be used in combination.

Analysis of Physical Characteristics of Olefin Polymer

The content of the copolymer component (rubber component, hereinafter abbreviated to "CP") prepared in the second step in the propylene-based polymer prepared in the presence of the catalyst according to the present invention and the proportion of ethylene or α-olefin units in the CP are determined by the following methods.

Although the proportion of ethylene units in the CP is determined in the following examples, the proportion of α-olefin units other than ethylene units may be determined as in the following examples.

(1) Analyzers Used (i) Cross-Fractionation Chromatograph

CFC T-100 from Dia Instruments Co., Ltd.

(ii) Fourier Transform Infrared Absorption Spectrometer (FT-IR)

1760X from PerkinElmer Inc.

A detector, i.e., a fixed-wavelength infrared spectrophotometer, attached to the cross-fractionation chromatograph (CFC) is replaced with the FT-IR.

The transfer line from the outlet for the eluate emerging from the CFC to the FT-IR has a length of 1 m and is maintained at 140° C. during the measurement. The flow cell attached to the FT-IR has an optical path length of 1 mm and an optical path width of 5 mm and is maintained at 140° C. during the measurement.

(iii) Gel Permeation Chromatograph (GPC)

Three GPC columns (AD806MS from Showa Denko K.K.) are connected in series downstream of the CFC.

(2) CFC Conditions (i) Solvent: o-dichlorobenzene (ODCB)

(ii) Sample concentration: 4 mg/mL (iii) Injection volume: 0.4 mL (iv) Crystallization: cooled from 140° C. to 40° C. over about 40 minutes.

(v) Fractionation

Three fractions are collected at 40° C., 100° C., and 140° C. in temperature-rising elution fractionation chromatography.

The proportions of the fraction eluted at 40° C. or lower (Fraction 1), the fraction eluted at 40° C. to 100° C. (Fraction 2), and the fraction eluted at 100° C. to 140° C. (Fraction 3) are defined as W40, W100, and W140, respectively (unit: % by weight), where W40+W100+W140=100. The resulting fractions are automatically transported to the FT-IR instrument.

(vi) Flow Rate of Solvent During Elution: 1 mL/Min (3) FT-IR Conditions

After the sample solution starts eluting from the GPC downstream of the CFC, FT-IR is performed to acquire GPC-IR data of Fractions 1 to 3 described above under the following conditions:

(i) Detector: mercury cadmium telluride (MCT)

(ii) Resolution: 8 $cm^{-1}$ (iii) Measurement interval: 0.2 minute (12 seconds)

(iv) Number of acquisitions for each measurement: 15

(4) Post-Processing and Analysis of Results

The amount and molecular weight distribution of the fraction eluted at each temperature are determined from an absorbance chromatogram at 2,945 cm$^{-1}$ by FT-IR. The amount of eluate is normalized with respect to the total amount of eluate (100%). The retention volume is converted into the molecular weight with a calibration curve created from polystyrene standards in advance. The polystyrene standards used are F380, F288, F128, F80, F40, F20, F10, F4, F1, A5000, A2500, and A1000 available from Tosoh Corporation.

The calibration curve is created by injecting 0.4 mL of a solution of each polystyrene standard in ODCB (containing 0.5 mg/mL BHT) in a concentration of 0.5 mg/mL. The calibration curve is determined by a cubic equation obtained by least-squares approximation. The retention volume is converted into the molecular weight using a general-purpose calibration curve in accordance with Sadao Mori, "Saizu Haijo Kuromatogurafi (Size Exclusion Chromatography)" (Kyoritsu Shuppan Co., Ltd.). The following values are assigned to the viscosity equation ($[\eta]=K\times M^{\alpha}$):

(i) For creation of calibration curve from polystyrene standards

K=0.000138, α=0.70

(ii) For measurements on sample propylene block copolymers

K=0.000103, α=0.78

The ethylene content distribution (the ethylene content versus the molecular weight) of each eluate is determined from the ratio of the absorbance at 2,956 cm$^{-1}$ to the absorbance at 2,927 cm$^{-1}$ of a GPC-IR spectrum using a calibration curve for conversion into the ethylene unit proportion (mol %) created in advance from polyethylene, polypropylene, an ethylene-propylene rubber (EPR) of which the ethylene content is known by a method such as $^{13}$C-NMR spectroscopy, and mixtures thereof.

(5) CP Content

The CP content of a propylene block copolymer in the present invention is defined by equation (I) and is determined through the following procedure:

$$\text{CP content (\% by weight)} = W40 \times A40/B40 + W100 \times A100/B100 \quad (I)$$

where W40 and W100 are the proportions (unit: % by weight) of the fractions described above; A40 and A100 are each the average of the observed ethylene contents (unit: % by weight) of the fraction corresponding to W40 or W100; and B40 and B100 are each the ethylene content (unit: % by weight) of the CP present in the corresponding fraction. The procedures for determination of A40, A100, B40, and B100 will be described later.

Equation (I) has the following meaning:

The first term on the right side of equation (I) indicates the amount of CP present in Fraction 1 (fraction soluble at 40° C.). If Fraction 1 contains only CP but not PP, W40 contributes directly to the content of CP derived from Fraction 1 in the entire eluate. Fraction 1, however, contains not only CP-derived components, but also small amounts of PP-derived components (components having extremely low molecular weights and atactic polypropylene), which facts represent the necessity of correction. Accordingly, W40 is multiplied by A40/B40 to calculate the amount of CP-derived components in Fraction 1. For example, from an average ethylene content (A40) of 30% by weight in Fraction 1 and an ethylene content (B40) of 40% by weight of the CP present in Fraction 1, $^{30}/_{40}=\frac{3}{4}$ of Fraction 1 (i.e., 75% by weight) is attributed to CP, whereas ¼ is attributed to PP.

Thus, the multiplication by A40/B40 in the first term on the right side corresponds to calculation of the contribution of CP from the weight percent (W40) of Fraction 1. The second term of the right side has a similar meaning. The CP content is the sum of the contributions of CP calculated for the individual fractions.

The average ethylene contents A40, A100, and A140 of Fractions 1 to 3 are determined as the sum of the product of the weight proportion at each data point in an absorbance chromatograph at 2,945 cm$^{-1}$ and the ethylene content at the data point (determined from the ratio of the absorbance at 2,956 cm$^{-1}$ to the absorbance at 2,927 cm$^{-1}$).

B40 is determined as the ethylene content (unit: % by weight) corresponding to the peak in the differential molecular weight distribution curve of Fraction 1.

In Fraction 2, B100 cannot be determined by the same definition because the entire rubber component dissolves at 40° C.; therefore, B100 is defined as 100 in the present invention. B40 and B100, which are the ethylene contents in CP present in the fractions, cannot experimentally be determined because no means is available for completely separating PP and CP present in the fractions.

Research on various model samples has revealed that improvements in physical properties can be reasonably explained if B40 is determined as the ethylene content corresponding to the peak in the differential molecular weight distribution curve of Fraction 1. B100 can be approximated to 100, which is close to the actual status and involves little computational error, because the fraction has crystallinity derived from ethylene chains and also because the amount of CP present in the fraction is small compared to the amount of CP present in Fraction 1. Accordingly, B100 is defined as 100 for analysis.

Thus, the CP content can be calculated by equation (II):

$$\text{CP content (\% by weight)} = W40 \times A40/B40 + W100 \times A100/100 \quad (II)$$

The first term on the right side of equation (II), i.e., W40×A40/B40, refers to the content (% by weight) of amorphous CP, and the second term, i.e., W100×A100/100, refers to the content (% by weight) of crystalline CP.

The ethylene content in the copolymer component is calculated from equation (III) with the content of the copolymer component calculated by equation (II):

$$\text{Ethylene content (\% by weight) in copolymer component} = (W40 \times A40 + W100 \times A100 + W140 \times A140)/[\text{copolymer component content (\% by weight)}] \quad (III)$$

The above three fractionation temperatures are established for the following reason.

In the CFC analysis according to the present invention, the temperature 40° C. is necessary and sufficient for fractionation of only amorphous polymers (e.g., the majority of CP, propylene polymer (PP) components having extremely low molecular weights, and atactic PP components). The temperature 100° C. is necessary and sufficient for elution of only components insoluble at 40° C. but soluble at 100° C. (e.g., crystalline CP components due to ethylene and/or propylene chains and lowly crystalline PP components). The temperature 140° C. is necessary and sufficient for elution of only components insoluble at 100° C. but soluble at 140° C. (e.g., highly crystalline PP components and CP components having extremely high molecular weights and significantly high ethylenic crystallinity) and for recovering the entire propylene block copolymer used for analysis.

W140 is excluded from the calculation of the CP content and the ethylene content because CP components are absent or present in extremely small and substantially negligible amounts.

(6) Proportion of Ethylene Units

The ethylene content in CP is calculated by the following equation:

Ethylene content (% by weight) in CP=($W40 \times A40 + W100 \times A100$)/[CP]

where [CP] is the CP content (% by weight) determined as described above.

The calculated ethylene content (% by weight) in CP is finally converted into the mole percent using the molecular weights of ethylene and propylene.

EXAMPLES

To further illustrate and clarify the invention, the invention will be described with reference to a comparison between the Examples and the Comparative Examples to demonstrate the validity and significance of the requirements of the present invention and its superiority to the related art.

In the following examples, all the synthesis of complexes and catalysts and polymerization steps were performed under a purified nitrogen atmosphere, and solvents were used after being dehydrated and then degassed by bubbling with purified nitrogen.

The measurement and analysis of physical properties in the examples were performed by the procedures described above and below.

(1) Measurement of MFR

A solution (6 g) of a heat stabilizer (BHT) (0.6% by weight) in acetone was added to a polymer (6 g).

After being dried, the polymer was charged into a melt indexer (230° C.) and was left under a load of 2.16 Kg for 5 minutes. The amount of polymer extruded was then measured. The MFR was defined as the amount of polymer extruded for 10 minutes (unit: g/10 min).

(2) Measurement of Melting Point (Tm)

A polymer was subjected to one cycle of heating and cooling in the range of 20° C. to 200° C. at 10° C./min with a DSC (TA2000 from DuPont or DSC6200 from Seiko Instruments Inc.). The melting point was measured during the second heating at 10° C./min.

(3) Measurement of CFC

The CFC was measured by the procedure described in detail above.

Example 1

Synthesis of Metallocene Complex A: Synthesis of Dimethylsilylene-Bis[2-(5-Methyl-2-Furyl)-4-Phenyl-5,6-Dimethylindenyl]Zirconium Dichloride (Metallocene Complex A)

(1-1) Synthesis of 5,6-Dimethylindanone

A mixture of 48 mL (0.4 mol) of o-xylene and 50 g of 3-chloropropionyl chloride was added dropwise to a suspension of 116 g (0.87 mol) of aluminum chloride in 200 mL of nitromethane on an ice bath. After the solution was warmed to room temperature and was stirred for 5 hours, the solution was poured into 1 N hydrochloric acid-ice water, and the mixture was stirred. The organic layer was separated, was washed with 1 N hydrochloric acid, water, and then saturated brine, and was dried over magnesium sulfate. The solvent was distilled off under reduced pressure while the precipitated solid content was collected as needed during the distillation. The solid content was gradually added to 300 mL of sulfuric acid. The mixture was heated in an oil bath at 100° C. with stirring for 4 hours. About 40% cyclic isomer byproduct was yielded. After the reaction, the solution was poured into ice water. The organic layer was extracted with diethyl ether, was washed with water and then saturated brine, and was dried over magnesium sulfate. The solvent was distilled off under reduced pressure. The resulting solid content was recrystallized from hot hexane to remove the cyclic isomer to give 25.5 g (40% yield) of 5,6-dimethylindanone.

$^1$H-NMR (400 MHz, CDCl$_3$): 2.26 (s, 3H, tol-Me), 2.35 (s, 3H, tol-Me), 2.66 (d, J=4 Hz, 2H, CH$_2$), 3.05 (d, J=4 Hz, 2H, CH$_2$), 7.25 (s, 1H, arm), 7.53 (s, 1H, arm)

(1-2) Synthesis of 4-Bromo-5,6-Dimethylindene

The resulting 5,6-dimethylindanone (25.5 g) was added to a suspension of aluminum chloride (49 g) in chloroform (250 mL). After the mixture was stirred at room temperature for 3 hours, 10 mL of a solution of 8.2 mL of bromine in chloroform was added dropwise under being cooled on an ice bath, and the mixture was reacted at room temperature for one day. After the reaction, the solution was poured into 1 N hydrochloric acid-ice water, and the mixture was stirred. The organic layer was separated, was washed with 1 N hydrochloric acid, water, and then saturated brine, and was dried over magnesium sulfate. The solvent was distilled off under reduced pressure. The solid content was washed with hexane. The resulting crude 4-bromo-5,6-dimethylindanone (33 g) was suspended in ethanol. Sodium borohydride (5.2 g) was added to the suspension under being cooled on an ice bath, and the mixture was stirred at room temperature for one day. After the reaction, about half the solvent was distilled off under reduced pressure. After 1 N hydrochloric acid was added to quench the reaction, the organic layer was extracted with diethyl ether, was washed with water and then saturated brine, and was dried over magnesium sulfate. The solvent was distilled off under reduced pressure to yield a yellow solid content. p-Toluenesulfonic acid (0.5 g) and toluene (250 mL) were added to the yellow solid content, and the mixture was heated under reflux. A half hour later, water was added, and then the organic layer was separated, was washed with saturated brine, and was dried over magnesium sulfate. The solvent was distilled off to yield a crude product. The crude product was purified by silica gel chromatography to yield 13 g (37% yield) of the target compound, i.e., 4-bromo-5,6-dimethylindene.

$^1$H-NMR (400 MHz, CDCl$_3$): 2.37 (s, 3H, tol-Me), 2.41 (s, 3H, tol-Me), 3.37 (s, 2H, CH$_2$), 6.51 (d, 1H, CH), 6.82 (d, 1H, CH), 7.14 (s, 1H, arm)

(1-3) Synthesis of 4-Phenyl-5,6-Dimethylindene

In 200 mL of anhydrous toluene were dissolved phenylboronic acid (5.7 g, 46.7 mmol), tripotassium phosphate n-hydrate (15.2 g), 4-bromo-5,6-dimethylindene (8 g, 36 mmol), palladium acetate (0.24 g, 1.1 mmol %), and biphenyldicyclohexylphosphine (0.75 g). The mixture was reacted by heating under reflux for 0.5 hour. The solution was poured into 1N hydrochloric acid-ice water. After the mixture was stirred, the organic layer was separated, was washed with saturated brine, and was dried over magnesium sulfate. The solvent was distilled off under reduced pressure.

The mixture was filtered through silica gel to yield crude 4-phenyl-5,6-dimethylindene (7.7 g).

(1-4) Synthesis of 2-Bromo-4-Phenyl-5,6-Dimethylindene

The crude 4-phenyl-5,6-dimethylindene (10.6 g, 48 mmol) was dissolved in dimethyl sulfoxide (120 mL), and water (4 mL) was added. N-Bromosuccinimide (11.1 g, 62 mmol) was added to the solution at 0° C., and the mixture was stirred at room temperature for 4 hours. After water was added to the mixture on an ice bath to quench the reaction, the organic layer was extracted with toluene. After p-toluenesulfonic acid monohydrate (0.2 g) was added to the organic layer, the mixture was reacted by heating under reflux for 2 hours. Water was added to the solution, and the organic layer was separated from the solution, was washed with saturated brine, and then was dried over magnesium sulfate. The solvent was distilled off under reduced pressure. The mixture was filtered through silica gel to yield a crude product (12.5 g).

(1-5) Synthesis of 2-(5-Methyl-2-Furyl)-4-Phenyl-5,6-Dimethylindene

In dimethoxyethane (100 mL) was dissolved 2-methylfuran (5.9 mL, 65.8 mmol). A solution of n-butyllithium in n-hexane (1.62 M, 40.4 mL) was added dropwise under being cooled on an ice bath. After the mixture was stirred for 2 hours, trimethyl borate (8.5 mL, 75 mmol) was added dropwise under being cooled on an ice bath, and the mixture was stirred at room temperature for 16 hours. Water (5 mL) was then added, and the solution was stirred for 1 hour. The solvent was distilled off under reduced pressure. To the mixture were added, in sequence, a solution (80 mL) of sodium carbonate (8.8 g) in water, a solution of the crude 2-bromo-4-phenyl-5,6-dimethylindene synthesized as described above (12.5 g) in dimethoxyethane (60 mL), and tetrakis(triphenylphosphine)palladium (1.2 g), and the mixture was reacted by heating under reflux for 2 hours. The solution was poured into 1N hydrochloric acid-ice water. The organic layer was separated, was washed with 1 N hydrochloric acid and then saturated brine, and was dried over magnesium sulfate. The solvent was distilled off under reduced pressure. The reaction product was recrystallized to yield the target compound, i.e., 2-(5-methyl-2-furyl)-4-phenyl-5,6-dimethylindene (7.3 g).

(1-6) Synthesis of Dimethyl-Bis[2-(5-Methyl-2-Furyl)-4-Phenyl-5,6-Dimethylindenyl]Silane In a mixture of diethyl ether (30 mL) and toluene (40 mL) was dissolved 2-(5-methyl-2-furyl)-4-phenyl-5,6-dimethylindene (2.4 g, 8.0 mmol). A solution of n-butyllithium in n-hexane (1.59 M, 5.0 mL) was added dropwise at −40° C. After the solution was warmed to room temperature and was stirred for 3 hours, N-methylimidazole (0.02 mL) and dichlorodimethylsilane (0.49 mL, 4.0 mmol) were added dropwise at −30° C. The mixture was warmed to room temperature and was stirred for 1.5 hours. Water was added to the mixture, and the organic layer was separated and was dried over magnesium sulfate. The solvent was distilled off under reduced pressure to yield crude dimethyl-bis{2-(5-methyl-2-furyl)-4-phenyl-5,6-dimethylindenyl}silane (2.6 g).

(1-7) Synthesis of Dimethylsilylene-Bis[2-(5-Methyl-2-Furyl)-4-Phenyl-5,6-Dimethylindenyl] Zirconium Dichloride (Metallocene Complex A)

The crude dimethyl-bis{2-(5-methyl-2-furyl)-4-phenyl-5,6-dimethylindenyl}silane (2.6 g) was dissolved in a mixture of diethyl ether (30 mL) and toluene (50 mL). A solution of n-butyllithium in n-hexane (1.59 M, 5.0 mL) was added dropwise to the solution on an ice bath. After the solution was stirred at room temperature for 3 hours, the solvent was distilled off under reduced pressure. The mixture was washed with hexane (40 mL) three times, and the solvent was distilled off under reduced pressure. The solid content was added to a suspension of zirconium tetrachloride (0.9 g) in methylene chloride (40 mL) at −72° C., and the mixture was stirred at the temperature for 2 hours and was then stirred at room temperature for 4 hours. The solution was concentrated and was subjected to extraction with toluene and then n-hexane. The organic layer was washed with n-hexane, diisopropyl ether, and then toluene. The reaction product was repeatedly recrystallized from methylene chloride-hexane to yield 0.3 g of a racemic mixture of dimethylsilylene-bis[2-(5-methyl-2-furyl)-4-phenyl-5,6-dimethylindenyl]zirconium dichloride.

$^1$H-NMR (400 MHz, CDCl$_3$): 1.09 (s, 6H, Si(CH$_3$)$_2$), 2.05 (s, 6H, tol-CH$_3$), 2.14 (s, 6H, tol-CH$_3$), 2.41 (s, 6H, furyl-CH$_3$), 6.02 (dd, J=1.0 Hz, 3.3 Hz, 2H, furyl-H), 6.16 (d, J=3.3 Hz, 2H, furyl-H), 6.44 (s, 2H, Cp), 6.67 (s, 2H, arm.), 7.09-7.12 (m, 2H, arm.), 7.28-7.37 (m, 2H, arm.), 7.43-7.50 (m, 2H, arm.), 7.67-7.72 (m, 2H, arm.)

(1-8) Treatment of Smectite Ion-Exchangeable Layered Silicate with Acid and Salt Acid Treatment Distilled water and (1,130 g) and 96% sulfuric acid (750 g) were placed into a separable flask, and the internal temperature was maintained at 90° C. Benclay SL (average particle size: 19 μm, 300 g), which is granulated montmorillonite available from Mizusawa Industrial Chemicals, Ltd., was placed into the flask, and the mixture was reacted for 2 hours. The suspension was cooled to room temperature over 1 hour and was washed with distilled water into a pH of 4. The washing ratio was not more than 1/10,000.

Salt Treatment

Lithium sulfate monohydrate (210 g) was dissolved in distilled water (520 g) in a separable flask. The filtered acid-treated clay was placed into the flask, and the mixture was stirred at room temperature for 120 minutes. The slurry was then filtered. Distilled water (3,000 mL) was added to the solid content, and the mixture was stirred at room temperature for 5 minutes. The slurry was then filtered. Distilled water (2,500 mL) was added to the solid content, and the mixture was stirred for 5 minutes. The slurry was then filtered again. This operation was repeated additional four times. The solid content was predried at 130° C. under a nitrogen stream for 2 days, and coarse particles with particle sizes of 53 μm or more were removed. The solid content was dried at 200° C. under reduced pressure for 2 hours to yield chemically treated montmorillonite.

(1-9) Preparation of Catalyst with Metallocene Complex A (Catalyst A)

The chemically treated montmorillonite (5.0 g) was weighed into a 1 L flask. Into the flask were placed 32 mL of heptane and a solution of triisobutylaluminum in heptane (17 mL, 12.5 mmol), and the mixture was stirred at room temperature for 1 hour. The mixture was then washed with heptane to a residual liquid content of 1/100. Finally, the slurry was adjusted to a volume of 50 mL. A solution (1.0 mL) of triisobutylaluminum in heptane was added to the slurry, and the slurry was stirred at room temperature for 10 minutes. A solution of Metallocene Complex A (122 mg, 150 μmol) in toluene (30 mL) was further added to the slurry, and the mixture was stirred at room temperature for 60 minutes.

Heptane (350 mL) was then added to the heptane slurry. The slurry was introduced into a 1 L stirring autoclave. Propylene was supplied at 40° C. at a constant rate of 5 g/hr for 120 minutes.

After the supply of polypropylene, the slurry was maintained at 50° C. for 2 hours. The residual gas was purged, and the prepolymerized catalyst slurry was recovered from the autoclave. The recovered prepolymerized catalyst slurry was left at rest, and then the supernatant was removed. A solution of triisobutylaluminum in heptane (4.3 mL, 3.0 mmol) was added to the remaining solid content at room temperature. After the mixture was stirred at room temperature for 10 minutes, the solid content was dried under reduced pressure to recover 13.4 g of a solid catalyst (Catalyst A). The prepolymerization ratio (the amount of prepolymer divided by the amount of solid catalyst) was 1.68.

(1-10) Block Copolymerization of Propylene-Propylene/Ethylene with Catalyst A [1-(1)]

First Step

A 3 L stirring autoclave was sufficiently purged with propylene. A solution of triisobutylaluminum in n-heptane (2.76 mL, 2.02 mmol) was placed into the autoclave. Hydrogen (200 mL) and then liquid propylene (750 g) were introduced into the autoclave, and the system was maintained at 65° C. Catalyst A was slurried with n-heptane, and 50 mg (excluding the weight of the prepolymer) of the catalyst was introduced to start polymerization. The internal temperature of the autoclave was maintained at 65° C. One hour after the introduction of the catalyst, the residual monomer was purged, and the autoclave was purged with argon. After stirring was stopped, a tube was inserted into the autoclave under an argon flow to extract a small amount of polypropylene.

Second Step

Propylene and ethylene in a molar ratio of 60:40 were introduced into a pressure of 1.8 MPa at an internal temperature of 60° C., and the internal temperature was raised to 80° C. While a gaseous mixture of propylene and ethylene prepared in advance was being introduced, the polymerization reaction was controlled at an internal pressure of 2.0 MPa for 30 minutes to yield 99.8 g of propylene-propylene/ethylene block copolymer with good particulate characteristics. The average molar ratio of polypropylene to ethylene in the autoclave during the copolymerization of propylene and ethylene was 59:41.

The results of CFC-IR spectroscopy showed that the resulting block copolymer had a rubber content (CP content) of 14 wt %, an ethylene content in the rubber (CP) of 32 mol %, and a weight average molecular weight (Mw) of the CP of 730,000. The rubber polymerization activity (CP activity) was 570 g-CP/g-Cat/hr. The propylene homopolymer separately sampled in the first step had a Tm of 159° C. and an MFR of 16 dg/min.

(1-11) Block Copolymerization of Propylene-Propylene/Ethylene with Catalyst A [1-(2)]

Steps (1-10) in Example 1 were repeated except that the average molar ratio of polypropylene to ethylene in the autoclave during the copolymerization of propylene and ethylene was adjusted to 45:55 to yield 64 g of a propylene-propylene/ethylene block copolymer. The separately sampled propylene homopolymer had a Tm of 159° C. and an MFR of 17 dg/min.

The results of CFC-IR spectroscopy showed that the resulting block copolymer had a rubber content (CP content) of 18 wt %, an ethylene content in the rubber (CP) of 48 mol %, and a weight average molecular weight (Mw) of the CP of 920,000. The rubber polymerization activity (CP activity) was 460 g-CP/g-Cat/hr.

Example 2

Synthesis of Metallocene Complex B: Synthesis of Dimethylsilylene-Bis[2-(5-Methyl-2-Furyl)-4-(4-t-Butylphenyl)-5,6-Dimethylindenyl]Zirconium Dichloride (Metallocene Complex B)

(2-1) Synthesis of 4-(4-t-Butylphenyl)-5,6-Dimethylindene

To a 500 mL three-necked flask were added 4-bromo-5,6-dimethylindene (3.4 g, 15 mmol), 4-t-butylphenylboronic acid (3.25 g, 18.2 mmol), tripotassium phosphate n-hydrate (7.7 g, 31 mmol), palladium acetate (0.11 g, 0.5 mmol), biphenyldicyclohexylphosphine (0.33 g, 0.94 mmol), and toluene (287 mL), and the mixture was heated under reflux in an oil bath for 2 hours. The solution was subjected to solvent separation and distillation to yield unpurified 4-(4-t-butylphenyl)-5,6-dimethylindene (4.6 g).

(2-2) Synthesis of 2-Bromo-4-(4-t-Butylphenyl)-5,6-Dimethylindene

Into a 500 mL recovery flask were placed the unpurified 4-(4-t-butylphenyl)-5,6-dimethylindene (4.6 g, 17 mmol), dimethyl sulfoxide (41 mL), and water (1.5 mL). N-Bromosuccinimide (5.04 g, 28.3 mmol) was then gradually added under ice cooling, and the mixture was stirred at room temperature for 3.5 hours. Toluene (100 mL) and water (100 mL) were then added at room temperature. The organic layer was extracted with toluene and was washed with water and then saturated brine. The organic layer was transferred to a 500 mL three-necked flask. p-Toluenesulfonic acid monohydrate (0.499 g, 2.62 mmol) was placed into the flask, and the mixture was heated under reflux in an oil bath for 1.5 hours. The solution was washed with an aqueous solution of sodium hydrogen carbonate and then saturated brine and was subjected to solvent separation and distillation to yield a yellowish brown oil of 2-bromo-4-(4-t-butylphenyl)-5,6-dimethylindene (5.4 g, 15 mmol).

(2-3) Synthesis of 2-(5-Methyl-2-Furyl)-4-(4-t-Butylphenyl)-5,6-Dimethylindene

Into a 200 mL Schlenk flask were placed 2-methylfuran (1.9 g, 23 mmol) and DME (21 mL). After the flask was cooled to −20° C., a solution of n-butyllithium in n-hexane (15.6 mL, 25 mmol, 1.63 M) was added dropwise. After the mixture was stirred for 1 hour, DME (21 mL) was added. Trimethyl borate (2.9 mL, 26 mmol) was added under ice cooling, and the mixture was stirred at room temperature for 1 hour. The solution was ice-cooled. Sodium carbonate (3.3 g, 31 mmol) and water (21 mL) were then added, and the mixture was stirred at room temperature for 1 hour. Half the solvent was removed under reduced pressure. To the solution were added 2-bromo-4-(4-t-butylphenyl)-5,6-dimethyl-indene (5.4 g, 15 mmol), tetrakis(triphenylphosphine) palladium (0.436 g, 0.377 mmol), DME (37 mL), and water (4.8 mL), and the mixture was heated under reflux in an oil bath for 2 hours. The solution was subjected to solvent separation and distillation and was purified by silica gel chromatography to yield a light orange solid of 2-(5-methyl-2-furyl)-4-(4-t-butylphenyl)-5,6-dimethylindene (2.7 g, 7.5 mmol) in 49% yield.

(2-4) Synthesis of Dimethyl-Bis[2-(5-Methyl-2-Furyl)-4-(4-t-Butylphenyl)-5,6-Dimethylindenyl] Silane To a 100 mL Schlenk flask were added 2-(5-methyl-2-furyl)-4-(4-t-butylphenyl)-5,6-dimethylindene (1.6 g, 7.5 mmol) and THF (23 mL). After the flask was cooled to −78° C., a solution of n-butyllithium in n-hexane (3.10 mL, 5.0 mmol, 1.63 M) was added dropwise. The solution was stirred at −78° C. for 30 minutes and was then stirred at room temperature for 3 hours. N-Methylimidazole (9.0 μL, 0.11 mmol) and THF (5.2 mL) were then added. After the mixture was cooled to −30° C., dimethyldichlorosilane (0.27 mL, 2.3 mmol) was added dropwise, and the mixture was stirred at −30° C. for 15 minutes and then at room temperature for 2 hours. The solution was subjected to solvent separation and distillation and was purified by silica gel chromatography to yield an orange solid of dimethyl-bis[2-(5-methyl-2-furyl)-4-(4-t-butylphenyl)-5,6-dimethylindenyl]silane (1.28 g, 1.66 mmol) in 74% yield.

(2-5) Synthesis of Dimethylsilylene-Bis[2-(5-Methyl-2-Furyl)-4-(4-t-Butylphenyl)-5,6-Dimethyl-indenyl]Zirconium Dichloride (Metallocene Complex B)

To $Et_2O$ (20 mL) was added dimethyl-bis[2-(5-methyl-2-furyl)-4-(4-t-butylphenyl)-5,6-dimethylindenyl]silane (1.3 g, 1.7 mmol). After the mixture was cooled to −78° C., a solution of n-butyllithium in n-hexane (2.3 mL, 3.8 mmol, 1.63 M) was added dropwise. After being stirred for 2.5 hours with gradual warming to 0° C., the solution was concentrated, and dichloromethane (40 mL) was added. After the mixture was cooled to −78° C., zirconium tetrachloride (0.40 g, 1.7 mmol) was added, and the mixture was stirred for one day with gradual warming to room temperature. The solvent was distilled off under reduced pressure to yield a yellowish brown solid of a mixture (1.8 g) containing a complex.

The organic layer was extracted from the mixture with hexane and then dichloromethane/hexane to yield an orange solid of a racemic mixture of dimethylsilylene-bis[2-(5-methyl-2-furyl)-4-(4-t-butylphenyl)-5,6-dimethylindenyl] zirconium dichloride (137 mg, 0.147 mmol) in 9% yield.

$^1$H-NMR (400 MHz, $C_6D_6$): 1.02 (s, 6H, $Me_2Si$), 1.14 (s, 18H, tBu), 1.93 (s, 6H, Ar-Me), 2.05 (s, 6H, Ar-Me), 2.12 (s, 6H, furyl-Me), 5.70 (d, 2H, J=3 Hz, furyl-H), 6.18 (d, 2H, J=3 Hz, furyl-H), 6.84 (s, 2H, Cp-H), 6.91 (s, 2H, Ar—H), 7.15 (d, 2H, J=8 Hz, Ar—H), 7.29 (d, 2H, J=8 Hz, Ar—H), 7.37 (d, 2H, J=8 Hz, Ar—H), 8.20 (d, 2H, J=8 Hz, Ar—H).

(2-6) Preparation of Catalyst with Metallocene Complex B (Catalyst B)

The chemically treated montmorillonite in Example 1 (10.0 g) was weighed into a 1 L three-necked flask. Into the flask were placed heptane (65 mL) and a solution of triisobutylaluminum in heptane (35 mL, 25.4 mmol), and the solution was stirred at room temperature for 1 hour. The mixture was then washed with heptane to a residual liquid content of 1/100. Finally, the slurry was adjusted to a volume of 100 mL.

A solution of triisobutylaluminum in heptane (1.7 mL, 1.2 mmol) was added to the slurry of triisobutylaluminum-treated montmorillonite in heptane prepared as described above. Into the 1 L three-necked flask was placed a solution (60 mL) of dimethylsilylene-bis[2-(5-methyl-2-furyl)-4-(4-t-butylphenyl)-5,6-dimethylindenyl]zirconium dichloride (137 mg, 147 μmol) in heptane, and the mixture was stirred at room temperature for 1 hour.

Heptane (340 mL) was then added to the slurry of montmorillonite in heptane. The slurry was introduced into a 1 L stirring autoclave. Propylene was supplied at 40° C. at a constant rate (10 g/h) over 2 hours. After the supply of polypropylene, the slurry was maintained at 50° C. for 2.5 hours. The residual gas was purged, and the prepolymerized catalyst slurry was recovered from the autoclave. The recovered prepolymerized catalyst slurry was left at rest, and then the supernatant was removed. A solution of triisobutylaluminum in heptane (4.3 mL, 3.0 mmol) was added to the remaining solid content at room temperature. After the solution was stirred at room temperature for 10 minutes, the solid content was dried under reduced pressure to recover 31.4 g of a solid catalyst (Catalyst B). The prepolymerization ratio (the amount of prepolymer divided by the amount of solid catalyst) was 2.09.

(2-7) Block Copolymerization of Propylene-Propylene/Ethylene with Catalyst B [2-(1)]

Steps (1-10) in Example 1 were repeated except that Catalyst A was replaced with 50 mg of Catalyst B, the average molar ratio of polypropylene to ethylene in the autoclave during the copolymerization of propylene and ethylene was adjusted to 54:46, and 300 mL of hydrogen was added to yield 93 g of a propylene-propylene/ethylene block copolymer. The separately sampled propylene homopolymer had a Tm of 158° C. and an MFR of 46 dg/min.

The results of CFC-IR spectroscopy showed that the resulting block copolymer had a rubber content (CP content) of 12 wt %, an ethylene content in the rubber (CP) of 38 mol %, and a weight average molecular weight (Mw) of the CP of 645,000. The rubber polymerization activity (CP activity) was 220 g-CP/g-Cat/hr.

(2-8) Block Copolymerization of Propylene-Propylene/Ethylene with Catalyst B [2-(2)]

Steps (1-10) in Example 1 were repeated except that Catalyst A was replaced with 70 mg of Catalyst B, the average molar ratio of polypropylene to ethylene in the autoclave during the copolymerization of propylene and ethylene was adjusted to 45:55, and 300 mL of hydrogen was added to yield 154 g of a propylene-propylene/ethylene block copolymer. The separately sampled propylene homopolymer had a Tm of 158° C. and an MFR of 49 dg/min.

The results of CFC-IR spectroscopy showed that the resulting block copolymer had a rubber content (CP content) of 22 wt %, an ethylene content in the rubber (CP) of 49 mol %, and a weight average molecular weight (Mw) of the CP of 1,090,000. The rubber polymerization activity (CP activity) was 490 g-CP/g-Cat/hr.

Comparative Example 1

Synthesis of Metallocene Complex X: Synthesis of Dimethylsilylene-Bis{2-(5-Methyl-2-Furyl)-4-Phenyl-5-Methylindenyl}Zirconium Dichloride (Metallocene Complex X)

(Comparative Step 1-1) Synthesis of Metallocene Complex X

Metallocene complex X was synthesized in accordance with the method disclosed in Example 1 of Japanese Unexamined Patent Application Publication No. 2010-163423 to yield a racemic mixture (purity: 99% or more).

(Comparative Step 1-2) Preparation of Catalyst with Metallocene Complex X (Catalyst X)

The resulting chemically treated montmorillonite (10.0 g) was weighed into a 1 L flask. Into the flask were placed 65 mL of heptane and a solution of triisobutylaluminum in heptane (35 mL, 25 mmol), and the mixture was stirred at room temperature for 1 hour. The mixture was then washed with heptane to a residual liquid content of 1/100. Finally, the slurry was adjusted to a volume of 100 mL. A solution of triisobutylaluminum in heptane (1.67 mL, 1.2 mmol) was added to the slurry, and the slurry was stirred at room temperature for 10 minutes. A solution of Metallocene Complex X (247 mg, 310 μmol) in toluene (60 mL) was further added to the slurry, and the slurry was stirred at room temperature for 60 minutes.

Heptane (340 mL) was then added to the heptane slurry. The slurry was introduced into a 1 L stirring autoclave. Propylene was supplied at 40° C. at a constant rate of 10 g/hr for 120 minutes.

After the supply of polypropylene, the slurry was maintained at 50° C. for 4 hours. The residual gas was purged, and the prepolymerized catalyst slurry was recovered from the autoclave. The recovered prepolymerized catalyst slurry was left at rest, and then the supernatant was removed. A solution of triisobutylaluminum in heptane (8.5 mL, 6.0 mmol) was added to the remaining solid content at room temperature. After the mixture was stirred at room temperature for 10 minutes, the solid content was dried under reduced pressure to recover 28.8 g of a solid catalyst. The prepolymerization ratio (the amount of prepolymer divided by the amount of solid catalyst) was 0.42.

(Comparative Step 1-3) Block Copolymerization of Propylene-Propylene/Ethylene with Catalyst X Steps (1-10) in Example 1 were repeated except that 300 mL of hydrogen was added during the polymerization of propylene in the first step and the average molar ratio of polypropylene to ethylene in the autoclave during the copolymerization of propylene and ethylene in the second step was adjusted to 54:46 to yield 45 g of a propylene-propylene/ethylene block copolymer.

The results of CFC-IR spectroscopy showed that the resulting block copolymer had a rubber content (CP content) of 18 wt %, an ethylene content in the rubber (CP) of 34 mol %, and a weight average molecular weight (Mw) of the CP of 508,000. The rubber polymerization activity (CP activity) was 340 g-CP/g-Cat/hr. The separately sampled propylene homopolymer had a Tm of 156° C. and an MFR of 94 dg/min.

Comparative Example 2

Synthesis of Metallocene Complex Y: Synthesis of Dimethylsilylene-Bis[2-(5-Methyl-2-Furyl)-4-Phenylindenyl]Zirconium Dichloride (Metallocene Complex Y)

(Comparative Step 2-1) Synthesis of Metallocene Complex Y

Metallocene complex Y was synthesized in accordance with the method disclosed in Example 1 of Japanese Unexamined Patent Application Publication No. 2002-128832 to yield a racemic mixture (purity: 99% or more).

(Comparative Step 2-2) Preparation of Catalyst with Metallocene Complex Y (Catalyst Y)

Steps (1-2) in Comparative Example 1 were repeated except that Metallocene Complex X was replaced with 223 mg (293 μmol) of Metallocene Complex Y to yield Catalyst Y.

The prepolymerization ratio (the amount of prepolymer divided by the amount of solid catalyst) was 1.80.

(Comparative Step 2-3) Block Copolymerization of Propylene-Propylene/Ethylene with Catalyst Y Steps (1-10) in Example 1 were repeated except that 300 mL of hydrogen was added during the polymerization of propylene in the first step and the average molar ratio of polypropylene to ethylene in the autoclave during the copolymerization of propylene and ethylene in the second step was adjusted to 43:57 to yield 173 g of a propylene-propylene/ethylene block copolymer. The separately sampled propylene homopolymer had a Tm of 154° C. and an MFR of 162 dg/min.

The results of CFC-IR spectroscopy showed that the resulting block copolymer had a rubber content (CP content) of 9 wt %, an ethylene content in the rubber (CP) of 51 mol %, and a weight average molecular weight (Mw) of the CP of 121,000. The rubber polymerization activity (CP activity) was 1,200 g-CP/g-Cat/hr.

Table 1 summarizes the results of the polymerization with Metallocene Complex A in Examples [1-(1)] and [1-(2)], the polymerization with Metallocene Complex B in Examples [2-(1)] and [2-(2)], and the polymerization with Metallocene Complexes X and Y in Comparative Examples 1 and 2.

TABLE 1

| Example | Complex | Ethylene content in gas during CP polymerization (mol %) | Ethylene content in CP (mol %) | CP polymerization activity (g-CP/g-Cat/hr) | Molecular weight of CP (Mw) | Melting point of propylene homopolymer (° C.) |
|---|---|---|---|---|---|---|
| 1-(1) | A | 41 | 32 | 570 | 730,000 | 159 |
| 1-(2) | A | 55 | 48 | 460 | 920,000 | 159 |
| 2-(1) | B | 46 | 38 | 220 | 645,000 | 158 |
| 2-(2) | B | 55 | 49 | 490 | 1,090,000 | 158 |
| Comparative Example 1 | X | 46 | 34 | 340 | 508,000 | 156 |
| Comparative Example 2 | Y | 57 | 51 | 1,200 | 121,000 | 154 |

Metallocene Complex A: dimethylsilylene-bis[2-(5-methyl-2-furyl)-4-phenyl-5,6-dimethylindenyl]zirconium dichloride Metallocene Complex B: dimethylsilylene-bis[2-(5-methyl-2-furyl)-4-(4-t-butylphenyl)-5,6-dimethylindenyl]zirconium dichloride Metallocene Complex X: dimethylsilylene-bis[2-(5-methyl-2-furyl)-4-phenyl-5-methylindenyl]zirconium dichloride Metallocene Complex Y: dimethylsilylene-bis[2-(5-methyl-2-furyl)-4-phenylindenyl]zirconium dichloride The results of polymerization in Table 1 demonstrate that a metallocene complex and a catalyst containing the metallocene complex according to the present invention have a higher ethylene uptake rate, produce a rubber component having a higher molecular weight, and facilitate manufacture of homopolypropylene having a higher melting point through homopolymerization of propylene, compared to traditional metallocene catalysts.

INDUSTRIAL APPLICABILITY

A metallocene complex, a catalyst containing the metallocene complex, and a method of olefin polymerization according to the present invention facilitate manufacture of a rubber component having a high molecular weight and efficient manufacture of a propylene-propylene/(ethylene or α-olefin) block copolymer having a high ethylene or α-olefin content in the rubber component. The metallocene complex, the catalyst containing the metallocene complex, and the method of olefin polymerization according to the present invention are also significantly useful for manufacture of homopolypropylene having a high melting point through homopolymerization of propylene.

The invention claimed is:

1. A metallocene complex represented by formula [I]:

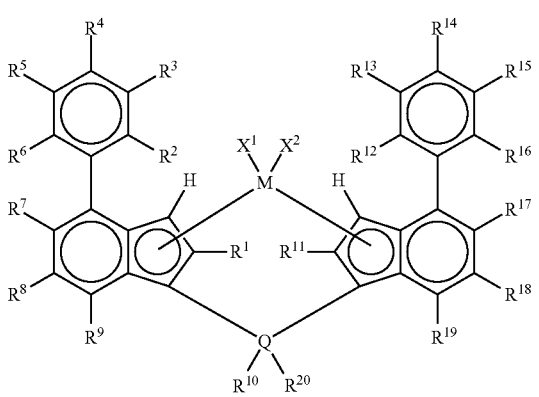

where M is titanium, zirconium, or hafnium;

Q is carbon, silicon, or germanium;

$X^1$ and $X^2$ are each independently a halogen atom, an alkyl group of 1 to 6 carbon atoms, an aryl group of 6 to 18 carbon atoms, an amino group substituted by an alkyl group of 1 to 6 carbon atoms, an alkoxy group of 1 to 6 carbon atoms, a halogenated alkyl group of 1 to 6 carbon atoms, or an halogenated aryl group of 6 to 18 carbon atoms;

$R^1$ and $R^{11}$ may be the same or different and are each a hydrogen atom, an alkyl group of 1 to 6 carbon atoms, an alkoxy group of 1 to 6 carbon atoms, a furyl group, a thienyl group, a substituted furyl group, or a substituted thienyl group, at least one of $R^1$ and $R^{11}$ being necessarily a furyl group, a thienyl group, a substituted furyl group, or a substituted thienyl group;

$R^8$ and $R^{18}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, an alkyl group of 1 to 6 carbon atoms having a trialkylsilyl group, a silyl group having a hydrocarbyl group of 1 to 6 carbon atoms, an aryl group of 6 to 18 carbon atoms, or a halogenated aryl group of 6 to 18 carbon atoms, where if either one of $R^8$ and $R^{18}$ is a hydrogen atom, the other one is not a hydrogen atom;

$R^2$, $R^3$, $R^4$, $R^5$, $R^6$, $R^9$, $R^{12}$, $R^{13}$, $R^{14}$, $R^{15}$, $R^{16}$, and $R^{19}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, an alkyl group of 1 to 6 carbon atoms having a trialkylsilyl group, an aryl group of 6 to 18 carbon atoms, a halogenated aryl group of 6 to 18 carbon atoms, a furyl group, a thienyl group, a substituted furyl group, or a substituted thienyl group, any adjacent two of $R^2$, $R^3$, $R^4$, $R^5$, $R^6$, $R^{12}$, $R^{13}$, $R^{14}$, $R^{15}$, and $R^{16}$ optionally forming a 5- to 7-membered ring, the 5- to 7-membered ring optionally containing an unsaturated bond;

$R^7$ and $R^{17}$ may be the same or different and are each an alkyl group of 1 to 6 carbon atoms, an alkoxy group of 1 to 6 carbon atoms, a halogenated alkyl group of 1 to 6 carbon atoms, or an alkyl group of 1 to 6 carbon atoms having a trialkylsilyl group; and $R^{10}$ and $R^{20}$ may be the same or different and are each an alkyl group of 1 to 6 carbon atoms, a halogenated alkyl group of 1 to 6 carbon atoms, an alkyl group of 1 to 6 carbon atoms having a trialkylsilyl group, a silyl group having a hydrocarbyl group of 1 to 6 carbon atoms, an aryl group of 6 to 18 carbon atoms, a halogenated aryl group of 6 to 18 carbon atoms, or an optionally substituted 5- or 6-membered heterocyclic group, $R^{10}$ and $R^{20}$ optionally forming a 4- to 7-membered ring, the 4- to 7-membered ring optionally containing an unsaturated bond.

2. The metallocene complex according to claim 1, wherein $R^8$ and $R^{18}$ in formula [I] may be the same or different and are each an alkyl group of 1 to 6 carbon atoms.

3. The metallocene complex according to claim 1, wherein $R^7$ and $R^{17}$ in formula [I] may be the same or different and are each an alkyl group of 1 to 6 carbon atoms.

4. The metallocene complex according to claim 1, wherein $R^2$, $R^6$, $R^9$, $R^{12}$, $R^{16}$, and $R^{19}$ in formula [I] are each a hydrogen atom.

5. The metallocene complex according to claim 1, wherein formula [I] is represented by formula [II]:

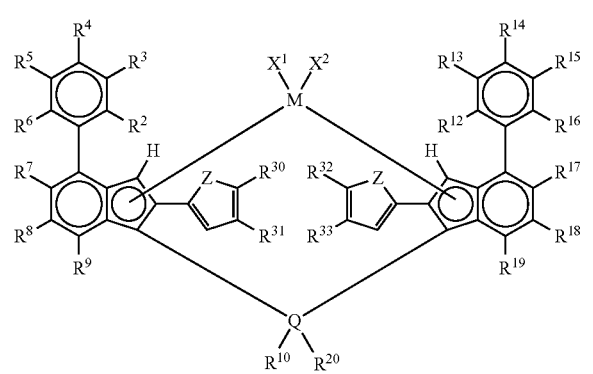

[II]

where Z is oxygen or sulfur; and
$R^{30}$, $R^{31}$, $R^{32}$, and $R^{33}$ may be the same or different and are each a hydrogen atom, a halogen atom, an alkyl group of 1 to 6 carbon atoms, an alkoxy group of 1 to 6 carbon atoms, a halogenated alkyl group of 1 to 6 carbon atoms, a silyl group having a hydrocarbyl group of 1 to 6 carbon atoms, or an aryl group of 6 to 18 carbon atoms, any adjacent two of $R^{30}$, $R^{31}$, $R^{32}$, and $R^{33}$ optionally forming a 5- to 7-membered ring, the 5- to 7-membered ring optionally containing an unsaturated bond.

6. An olefin polymerization catalyst comprising the metallocene complex according to claim 1.

7. An olefin polymerization catalyst comprising the following components:
(A) the metallocene complex according to claim 1;
(B) a compound reactive with the component (A) to form an ion pair or an ion-exchangeable layered silicate; and
(C) an organoaluminum compound.

8. The olefin polymerization catalyst according to claim 7, wherein the component (B) is an ion-exchangeable layered silicate.

9. A method for manufacturing a propylene-based polymer through two-step polymerization, the method comprising the steps of, in the presence of the olefin polymerization catalyst according to claim 7:
(i) polymerizing 90% to 100% by weight propylene and 0% to 10% by weight ethylene or α-olefin, based on the total weight of the monomer components; and
(ii) polymerizing 10% to 90% by weight propylene and 10% to 90% by weight ethylene and/or α-olefin of 4 or more carbon atoms, based on the total weight of the monomer components.

10. The method for manufacturing a propylene-based polymer through two-step polymerization according to claim 9, wherein
the first step comprises (i) polymerizing 90% to 100% by weight propylene and 0% to 10% by weight ethylene or α-olefin, based on the total weight of the monomer components, by bulk polymerization in which propylene functions as a solvent or by gas-phase polymerization in which the monomers are maintained in gaseous form, and
the second step comprises (ii) polymerizing 10% to 90% by weight propylene and 10% to 90% by weight ethylene or α-olefin, based on the total weight of the monomer components, by gas-phase polymerization.

* * * * *